United States Patent
Persillon et al.

(10) Patent No.: US 10,738,291 B2
(45) Date of Patent: Aug. 11, 2020

(54) VARIANTS OF EXOGLUCANASES HAVING IMPROVED ACTIVITY AND USES THEREOF

(71) Applicants: IFP Energies nouvelles, Rueil Malmaison (FR); Proteus, Longjumeau (FR); CENTRE NATIONAL DE LA RECHERCHE SCIENTIFIQUE—CNRS, Paris (FR)

(72) Inventors: Cecile Persillon, Nimes (FR); Christophe Ullmann, Nimes (FR); Celine Ayrinhac, Domessargues (FR); Olivier Bonzom, Nimes (FR); Antoine Margeot, Paris (FR); Hugues Mathis, Bussy Saint Georges (FR); Sebastien Fort, Vaulnaveys-le-Hau (FR); Sylvie Armand, Grenoble (FR); Stephanie Pradeau, Saint-Honore (FR)

(73) Assignees: IFP Energies nouvelles, Rueil Malmaison (FR); Proteus, Longjumeau (FR); CENTRE NATIONAL DE LA RECHERCHE SCIENTIFIQUE-CNRS, Paris (FR)

( * ) Notice: Subject to any disclaimer, the term of this patent is extended or adjusted under 35 U.S.C. 154(b) by 495 days.

(21) Appl. No.: 15/320,433

(22) PCT Filed: Jun. 12, 2015

(86) PCT No.: PCT/FR2015/051557
§ 371 (c)(1),
(2) Date: Dec. 20, 2016

(87) PCT Pub. No.: WO2015/193588
PCT Pub. Date: Dec. 23, 2015

(65) Prior Publication Data
US 2017/0152498 A1    Jun. 1, 2017

(30) Foreign Application Priority Data

Jun. 20, 2014   (FR) .................................... 14 55701

(51) Int. Cl.
| | | |
|---|---|---|
| *C12N 9/42* | (2006.01) | |
| *C12P 7/10* | (2006.01) | |
| *C12P 19/14* | (2006.01) | |
| *C12P 19/02* | (2006.01) | |

(52) U.S. Cl.
CPC .............. *C12N 9/2437* (2013.01); *C12P 7/10* (2013.01); *C12P 19/02* (2013.01); *C12P 19/14* (2013.01); *C12Y 302/01091* (2013.01); *Y02E 50/16* (2013.01)

(58) Field of Classification Search
None
See application file for complete search history.

(56) References Cited

FOREIGN PATENT DOCUMENTS

| FR | 2 782 323 A1 | 2/2000 |
|---|---|---|
| WO | WO-2012149403 A1 * | 11/2012 |
| WO | 2014/078546 A2 | 5/2014 |
| WO | 2014081884 A1 | 5/2014 |

OTHER PUBLICATIONS

Whisstock et al. Quaterly Reviews of Biophysics, 2003, "Prediction of protein function from protein sequence and structure", 36(3): 307-340.*
Witkowski et al. Conversion of a beta-ketoacyl synthase to a malonyl decarboxylase by replacement of the active-site cysteine with glutamine, Biochemistry. Sep. 7, 1999;38(36):11643-50.*
The International Search Report (ISR) for PCT/FR2015/051557 dated Aug. 26, 2015, pp. 1-3.
The Written Opinion of the International Searching Authority for PCT/FR2015/051557 dated Aug. 26, 2015, pp. 1-12.
Database Gene seq [Online] Jul. 17, 2014 (Jul. 17, 2014) "Fungal cellobiohydrolase II (CBH II) catalytic domain variant A438L.", XP002732775, retrieved from EBI accession No. GSP:BBG53179 Database accession No. BBG53179.
Database Geneseq [Online] Dec. 20, 2012 (Dec. 20, 2012) "Nectria haematococca mpVI 77-13-4 protein. SEQ 13." XP002732776, retrieved from EBI accession No. GSP:BAG13688 Database accession No. BAG13688.
Database Geneseq [Online] Jan. 22, 2009 (Jan. 22, 2009) "Lignocellulosic enzyme sequence. SEQ ID 282."., XP002732777 retrieved from EBI accession No. GSP:ASR93979 Database accession No. ASR93979.
Cuomo, et al., "Pathogen Specialization", Science, vol. 317, Issue 5843, pp. 1400-1402, Sep. 7, 2007(abstract).
Database Geneseq [Online] Jul. 17, 2014 (Jul. 17, 2014) "Nectria haematococca polypeptide, SEQ ID 20732." extrait de EBI accession No. GSP:BBH00383, Database accession No. BBH00383; http://ibis.internal.epo.org/exam/dbfetch.jsp?id=UNIPROT:IIRIJI dated Feb. 7, 2019.

* cited by examiner

*Primary Examiner* — Iqbal H Chowdhury
(74) *Attorney, Agent, or Firm* — McDonnell Boehnen Hulbert & Berghoff LLP

(57) ABSTRACT

The present invention relates to the expression and optimisation of enzymes involved in the breakdown of lignocellulosic biomass. The present invention relates to variants of the exoglucanase 2 of *Trichoderma reesei*, as well as to the use of said variants with improved efficiency in methods for breaking down cellulose and for producing biofuel.

7 Claims, 1 Drawing Sheet
Specification includes a Sequence Listing.

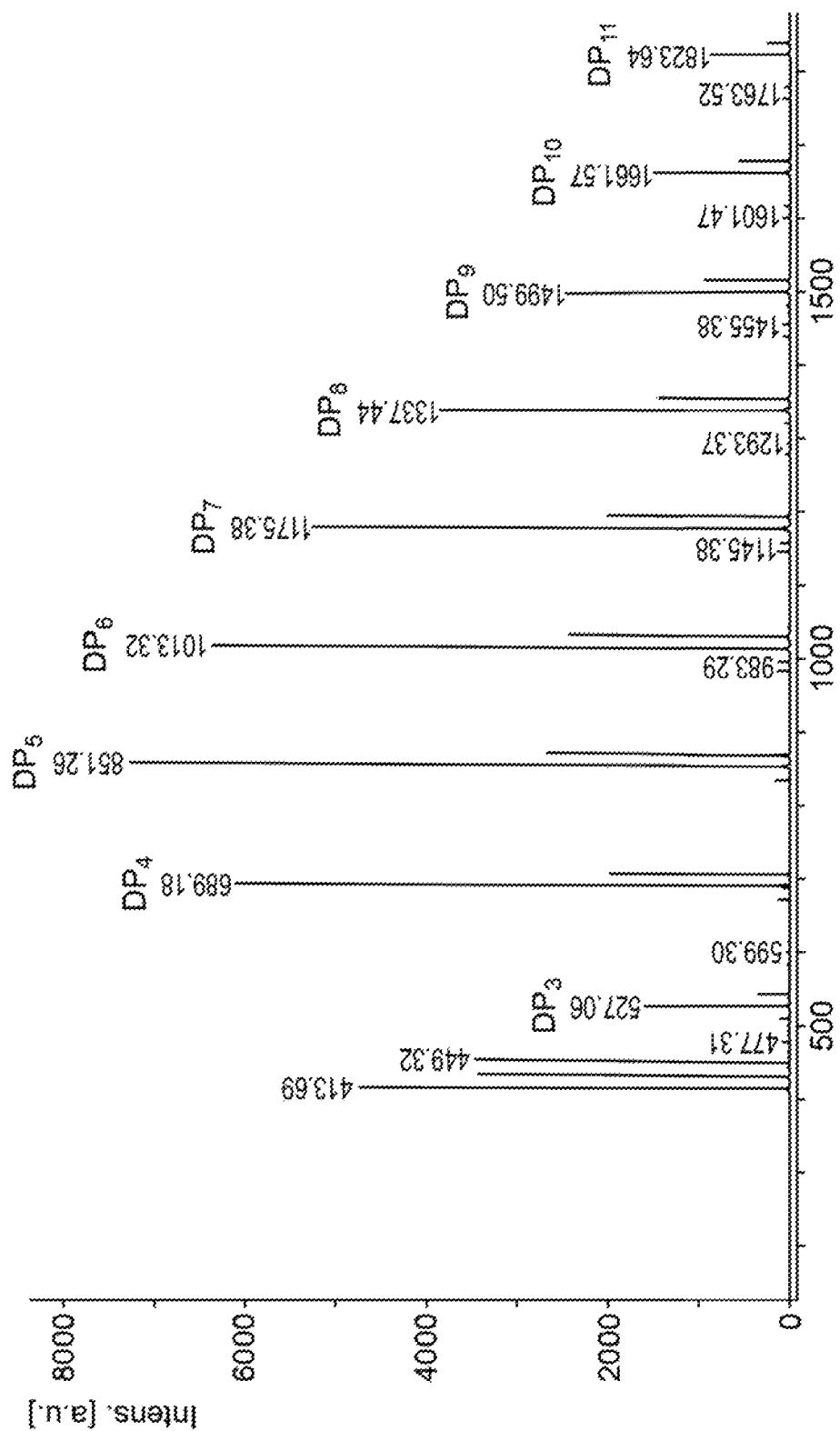

VARIANTS OF EXOGLUCANASES HAVING IMPROVED ACTIVITY AND USES THEREOF

The application is a U.S. national phase of International Application No. PCT/FR2015/051557, file Jun. 12, 2015, which claims priority from French Patent application no. Fr. 1455701, filed Jun. 20, 2014, the disclosure of each of which is hereby incorporated by reference in its entirety.

The possibility of producing ethanol from cellulose has received a great deal of attention owing to the availability of large amounts of raw material and also to the advantage of ethanol as a fuel. Cellulose-based natural raw materials for such a process are denoted "biomass". Many types of biomass, for example wood, agricultural residues, herbaceous crops and municipal solid waste, have been considered as potential raw materials for biofuel production. These materials consist mainly of cellulose, hemicellulose and lignin.

Cellulose is a polymer consisting of glucose molecules linked by beta 1,4 linkages, which are very resistant to breakdown or to depolymerization. Once cellulose has been converted to glucose, the latter is easily fermented to biofuel, for example ethanol, using a yeast.

The oldest methods studied for converting cellulose to glucose are based on acid hydrolysis. This process can be carried out in the presence of concentrated or dilute acids. However, several drawbacks, such as the poor recovery of the acid when concentrated acids are used and the low production of glucose in the context of the use of dilute acids, are detrimental to the economic nature of the acid hydrolysis process.

In order to overcome the drawbacks of the acid hydrolysis process, cellulose conversion processes have more recently related to enzymatic hydrolysis, using enzymes of cellulase type. This enzymatic hydrolysis of lignocellulosic biomass (for example, cellulose) has, however, the drawback of being an expensive industrial process. As a result, it is necessary to use increasingly effective cellulase-secreting microorganism strains. In this respect, many microorganisms comprise enzymes which hydrolyze cellulose, such as the fungi *Trichoderma*, *Aspergillus*, *Humicola* or *Fusarium* and also bacteria such as *Thermomonospora*, *Bacillus*, *Cellulomonas* and *Streptomyces*. The enzymes secreted by these microorganisms possess three different types of activity that are of use in the conversion of cellulose to glucose and can be divided into three groups: endoglucanases, which randomly attack cellulose fibers internally, exoglucanases which will attack the ends of the fibers, releasing cellobiose, and beta-glucosidases which will hydrolyze this cellobiose to glucose. Other classes of enzymes, such as hemicellulases or the recently discovered class of enzymes of polysaccharide monooxygenases, can also play a role in the efficiency of hydrolysis.

There is a strong industrial interest in decreasing the cost of enzymatic hydrolysis, and this decrease involves the use of a reduced dose of enzymes and thus of cocktails of enzymes that are more efficient. Consequently, several patent applications describe natural enzymes with capacities that are greater than those of *Trichoderma reesei*, or variants improved by genetic engineering. Mention may be made of patent applications US2010304464, WO 2010/066411 and WO 2013/029176 relating to exoglucanses, applications WO 2007/109441, WO 2012/149192 and WO 2010/076388 relating to endoglucanases, applications WO 2010/029259, WO 2010/135836 or WO 2010/022518 relating to beta-glucosidases, or else applications WO 12135659 and WO 12149344 relating to polysaccharide monooxygenases.

Enzymes which hydrolyze lignocellulosic biomass are classified in the CAZy system (Cantarel, B. L., Coutinho,P. M., Rancurel, C., Bernard, T., Lombard, V., & Henrissat, B. (2009). The Carbohydrate-Active EnZymes database (CAZy): an expert resource for Glycogenomics. Nucleic acids research, 37, D233-8) on the basis of mainly structural criteria. Exoglucanases can belong to the GH 6, 7, 9, 48 and 74 families.

In order for lignocellulosic biomass hydrolysis to be efficient and economically profitable, the enzymatic mixture must comprise balanced proportions of enzymes having various enzymatic activities, inter alia, but not exclusively, of the exoglucanase, endoglucanase, xylanase and beta-glucosidase type. By way of example, in the native mixtures of *Trichoderma reesei*, the presence of 60-70% of exoglucanases, 15-20% of endoglucanases, a few percent of hemicellulases and approximately 5-10% of beta-glucosidases is generally noted. This mixture is suitable for hydrolyzing the majority of pretreated substrates (for example of the type wheat straw steam-exploded under acid conditions) with acceptable yields. The already considerable proportion of exoglucanases in the mixture indicates that it will be difficult to increase the amount of these enzymes without penalizing the other activities. The *Trichoderma reesei* genome comprises two exoglucanases, one derived from family 6 (CBH2, cel6a) and the other derived from family 7 (CBH1, Cel7a). They hydrolyze to cellobiose respectively the non-reducing (EC3.2.1.176) and reducing (EC3.2.1.91) ends of cellulose.

The hydrolysis and the fermentation can be carried out according to various schemes. The most common consists of separate hydrolysis and fermentation (SHF). This method makes it possible to optimize each step by maintaining the optimal reaction conditions. This fermentation is carried out extemporaneously, at a temperature of between approximately 28° C. and approximately 30° C., whereas the hydrolysis generally takes place at a temperature of at least 45° C. However, in SHF, the sugars released at the end of the reaction are present at very high concentration and cause inhibition of the enzymes, slowing down the efficiency of the process. In order to avoid these drawbacks, another type of process can be envisioned. In SSF, the two steps (hydrolysis and fermentation of hexoses) take place simultaneously, preventing sugar accumulation at concentrations that are inhibitory for the enzymes. The investment costs are also reduced by virtue of the use of a single reactor. The rate of hydrolysis is higher as a consequence of the absence of inhibition, since the sugars released are used immediately for fermentation to ethanol. In this method, the temperature of the reactor necessarily constitutes a compromise between the optimal temperatures of hydrolysis and of fermentation, typically between approximately 30° C. and approximately 35° C. However, at such a temperature, the activity of the cellulolytic enzymes is decreased by approximately 30%.

SSF also allows the expression of enzymes that degrade cellulose in the organism fermenting the sugars, thereby making it possible to limit, or in an extreme case to eliminate, recourse to enzymes produced during a separate step.

Consequently, the obtaining of enzymes which maintain an exoglucanase activity that is efficient at the optimal temperatures of hydrolysis and fermentation (i.e. between 30° C. and 50° C.), while at the same time keeping the proportion of all of the enzymes of the mixture, would be a significant gain for the process of converting lignocellulosic biomass to biofuel.

The inventors have developed a polypeptide having an improved exoglucanase activity, in particular compared with the exoglucanase activity of the CBH2 reference protein of sequence SED ID NO: 2. CBH2 corresponds to exoglucanase 2 from *Trichoderma reesei*.

In this perspective, the applicants have, to their great credit, found, after numerous research studies, an isolated or purified polypeptide having an improved exoglucanase activity compared with the exoglucanase activity of the CBH2 reference protein (SEQ ID NO: 2).

The invention thus relates to a polypeptide chosen from the group consisting of:

i. an amino acid sequence chosen from SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26 and SEQ ID NO: 28; and ii. an amino acid sequence having a percentage of residues that are identical compared with the sequence SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26 and SEQ ID NO: 28 (percentage identity), of at least 70%, preferentially of at least 75%, 80%, 85%, 90%, 95%, 98% or 99%.

Preferably, the polypeptide as described above is characterized in that its expression in a fermentative organism is at least equal to the expression of the CBH2 reference protein (SEQ ID NO: 2).

According to the invention, the percentage identity of a given sequence relative to SEQ ID NO: 4, 6, 8, 10, 12, 14, 16, 18, 20, 22, 24, 26 or 28 corresponds to the number of residues that are identical between this given sequence and SEQ ID NO: 4, 6, 8, 10, 12, 14, 16, 18, 20, 22, 24, 26, or 28, divided by the number of residues in SEQ ID NO: 4, 6, 8, 10, 12, 14, 16, 18, 20, 22, 24, 26 or 28.

In one preferred embodiment, the polypeptide of the invention has an exoglucanase activity which is improved by at least 10%, preferentially by at least 20%, preferentially by at least 30%, even more preferentially by at least 40%, at a temperature of approximately 35° C. and/or of approximately 50° C., compared with the exoglucanase activity of the CBH2 polypeptide of amino acid sequence SEQ ID NO: 2.

Those skilled in the art will for example be able to determine the increase or in other words the improvement in the enzymatic activity either using a substrate such as the cellulose Avicel®, the cellulose PASC or with a chromogenic substrate (p-nitrophenyl glycoside), for example pNP lactoside. The enzymatic activity will be respectively revealed by colorimetric assay of the reducing sugars or else of the nitrophenol released.

An example of a protocol that those skilled in the art will be able to use for determining whether a polypeptide according to the invention has an enzymatic activity that is improved compared with that of the CBH2 reference protein (SEQ ID NO: 2), is the following:

preparation of a stock culture of *Y. lipolytica* expressing a recombinant enzyme according to the invention, overnight at 28° C.;
inoculation of an expression medium with a volume of stock culture making it possible to have an optical density at 600 nm equal to 0.2 at the beginning of culture;
culture of said cells at 28° C. for 96 hours;
centrifugation at 8000 rpm for 5 minutes;

incubation of 100 µl of supernatant with 100 µl of 0.1 M citrate phosphate buffer, pH 6, containing 1% of reduced cellodextrins (CDs), for 4 hours at 35° C. and 50° C.;
removal of 100 µl of reaction;
addition of 100 µl of DNS reagent;
incubation for 5 minutes at 100° C.;
incubation for 3 minutes on ice;
centrifugation for 10 minutes at 3000 rpm;
reading of the OD at 540 nm on 150 µl.

A subject of the invention is also a purified or isolated nucleic acid encoding at least one polypeptide as described above. Table 1 below comprises the identifications of the nucleic and peptide sequences for the reference gene CBH2 from *T. reesei*, the putative exoglucanases from *Nectria haematococca* (NH) and from *Giberella zeae* (GZ), and also for the polypeptides and nucleotides of the invention.

TABLE 1

| Clones | Nucleic acid | Polypeptide |
|---|---|---|
| CBH2 (wild-type) | SEQ ID NO: 1 | SEQ ID NO: 2 |
| 35B7 | SEQ ID NO: 3 | SEQ ID NO: 4 |
| 95B7 | SEQ ID NO: 5 | SEQ ID NO: 6 |
| 100F11 | SEQ ID NO: 7 | SEQ ID NO: 8 |
| 139F12 | SEQ ID NO: 9 | SEQ ID NO: 10 |
| 157B11 | SEQ ID NO: 11 | SEQ ID NO: 12 |
| 161A1 | SEQ ID NO: 13 | SEQ ID NO: 14 |
| 161C12 | SEQ ID NO: 15 | SEQ ID NO: 16 |
| 189H8 | SEQ ID NO: 17 | SEQ ID NO: 18 |
| 196D9 | SEQ ID NO: 19 | SEQ ID NO: 20 |
| 198E11 | SEQ ID NO: 21 | SEQ ID NO: 22 |
| 251B4 | SEQ ID NO: 23 | SEQ ID NO: 24 |
| 251C4 | SEQ ID NO: 25 | SEQ ID NO: 26 |
| 382A2 | SEQ ID NO: 27 | SEQ ID NO: 28 |
| GZ gene | SEQ ID NO: 29 | SEQ ID NO: 30 |
| NH-7 gene | SEQ ID NO: 31 | SEQ ID NO: 32 |

A subject of the invention is also a purified or isolated nucleic acid encoding at least one polypeptide as described above.

Preferably, said purified or isolated nucleic acid can be chosen from the following sequences: SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25 and SEQ ID NO: 27.

According to the invention, the nucleic acid as described above may be functionally linked to a promoter, a terminator or any other sequence required for its expression in a host cell.

The invention also relates to a vector comprising at least one nucleic acid as described above.

According to the invention, the term "vector" is intended to mean any DNA sequence into which it is possible to insert foreign nucleic acid fragments, the vectors making it possible to introduce foreign DNA into a host cell. As vectors, mention may be made, non-exhaustively, of: plasmids, cosmids, yeast artificial chromosomes (YACs), bacterial artificial chromosomes (BACs), P1 bacteriophage-derived artificial chromosomes (PACs) or virus-derived vectors.

The vector according to the invention may also carry a selectable marker. The term "selectable marker" is intended to mean a gene of which the expression confers on the cells that contain it a characteristic making it possible to select them. It is for example an antibiotic resistance gene.

A subject of the invention is also an isolated host cell comprising either at least one of the polypeptides as described above, or at least one of the nucleic acids as described above, or at least one of the vectors as described above.

Those skilled in the art will be able to introduce one of the polypeptides, one of the nucleic acids or one of the vectors as described above into the host cell by well-known conventional methods. For example, mention may be made of calcium chloride treatment, electroporation, and the use of a particle gun.

According to one embodiment, those skilled in the art will be able to introduce, into the host cell and by conventional methods, several copies of a nucleic acid encoding a polypeptide having an improved exoglucanase activity according to the invention.

According to one embodiment, the isolated host cell as described above is chosen from *Trichoderma, Aspergillus, Neurospora, Humicola, Myceliophthora, Chrysosporium, Penicillium, Fusarium, Thermomonospora, Bacillus, Pseudomonas, Escherichia, Clostridium, Cellulomonas, Streptomyces, Yarrowia, Pichia* and *Saccharomyces*.

According to one preferred embodiment, the isolated host cell as described above is chosen from *Trichoderma reesei, Trichoderma viridae, Trichoderma koningii, Aspergillus niger, Aspergillus nidulans, Aspergillus wentii, Aspergillus oryzae, Aspergillus phoenicis, Myceliophthora thermopila, Chrysosporium lucknowense, Neurospora crassa, Humicola grisae, Penicillium pinophilum, Penicillium oxalicum, Escherichia coli, Clostridium acetobutylicum, Clostridium saccharolyticum, Clostridium benjerinckii, Clostridium butylicum, Pichia pastoris, Yarrowia lipolityca* and *Saccharomyces cerevisiae*.

According to one preferred embodiment, the isolated host cell as described above is chosen from *Trichoderma reesei* and *Saccharomyces cerevisiae*.

A subject of the invention is also the use of any one of the polypeptides described above, for cellulose hydrolysis.

A subject of the invention is also the use of any one of the polypeptides described above, for biofuel production.

According to the invention, the term "biofuel" can be defined as being any product resulting from the conversion of biomass and that can be used for energy purposes. Firstly, and without wishing to be limited thereto, mention may be made, by way of example, of biogases, products that can be incorporated (optionally after subsequent conversion) into a fuel or which can be a fuel in their own right, such as alcohols (ethanol, butanol and/or isopropanol depending on the type of fermentative organism used), solvents (acetone), acids (butyric), lipids and their derivatives (short-chain or long-chain fatty acids, fatty acid esters), and also hydrogen.

Preferably, the biofuel according to the invention is an alcohol, for example ethanol, butanol and/or isopropanol. More preferentially, the biofuel according to the invention is ethanol.

In another embodiment, the biofuel is biogas.

In another embodiment, the product is a molecule that is advantageous in the chemical industry, for instance another alcohol, such as 1,2-propanediol, 1,3-propanediol, 1,4-propanediol or 2,3-butanediol, organic acids such as acetic acid, propionic acid, acrylic acid, butyric acid, succinic acid, malic acid, fumaric acid, citric acid or itaconic acid, or hydroxy acids such as glycolic acid, hydroxypropionic acid or lactic acid.

An embodiment for producing an enzymatic cocktail that is of use for lignocellulose hydrolysis is described below.

The strains of filamentous fungi, preferably *Trichoderma*, more preferentially *T. reesei*, capable of expressing at least one polypeptide according to the invention are cultured in fermenters, in the presence of a carbon-based substrate, such as lactose or glucose, chosen for the growth of the microorganism. In one embodiment, this carbon-based substrate, depending on its nature, is introduced into the fermenter before sterilization or is sterilized separately and introduced into the fermenter after sterilization of the latter so as to obtain an initial concentration of 20 to 35 g/l.

An aqueous solution containing the substrate chosen for the enzyme production is then added. An enzymatic composition which acts on lignocellulosic biomass, produced by the fungi is finally recovered by filtration of the culture medium. This composition contains in particular the beta-glucosidase, the endoglucanase and the exoglucanase according to the invention.

In one embodiment, the aqueous solvent containing the substrate chosen for the enzyme production is prepared at the concentration of 200-250 g/l. This solution also preferably contains an inducer substrate such as lactose. This aqueous solution is injected after exhaustion of the initial carbon-based substrate so as to provide an optimized amount, of between 35 and 45 mg/g of cells (fed batch). During this fed batch phase, the residual concentration of sugar in the culture medium is less than 1 g/l and the enzymes which act on lignocellulosic biomass are secreted by the fungus. Said enzymes can be recovered by filtration of the culture medium.

A subject of the invention is an enzymatic composition capable of acting on lignocellulosic biomass, said enzymatic composition being produced by filamentous fungi and comprising at least one polypeptide having an improved exoglucanase activity compared with the exoglucanase activity of the CBH2 reference protein. The term "filamentous fungi" is intended to mean in particular *Trichoderma*, more preferentially *T. reesei*.

Finally, a subject of the invention is a process for producing biofuel from biomass, comprising the following successive steps:

the biomass to be hydrolyzed is suspended in an aqueous phase;

the lignocellulosic biomass is hydrolyzed in an presence of an enzymatic composition as described above so as to produce a hydrolysate containing glucose;

the glucose of the hydrolysate is fermented in the presence of a fermentative organism so as to produce a fermentation must;

the biofuel is separated from the fermentation must.

In one embodiment, the biomass to be hydrolyzed is suspended in an aqueous phase in an amount of from 6% to 40% of solids, preferably 20% to 30%. The pH is adjusted to between 4 and 5.5, preferably between 4.8 and 5.2, and the temperature to between 40 and 60° C., preferably between 45 and 50° C. The hydrolysis reaction is initiated by adding the enzymatic composition which acts on lignocellulosic biomass; the amount normally used is from 10 to 30 mg of excreted proteins per gram of pretreated substrate or less. The reaction generally lasts from 15 to 48 hours. The reaction is followed by assaying of the sugars released, in particular glucose. The sugar solution is separated from the non-hydrolyzed solid fraction, essentially consisting of lignin, by filtration or centrifugation and then treated in a fermentation unit.

After the fermentation step, the biofuel is separated from the fermentation must for example by distillation.

Another subject of the invention is a process for producing biofuel from biomass, characterized in that it comprises the following successive steps:

the biomass to be hydrolyzed is suspended in an aqueous phase;

an enzymatic composition which acts on lignocellulosic biomass as defined above and a fermentative organism are simultaneously added to the suspension and the mixture is fermented so as to produce a fermentation must;

the biofuel is separated from the fermentation must.

Preferably, the enzymatic composition and the fermentative organism are added simultaneously and then incubated at a temperature of between 30° C. and 35° C. so as to produce a fermentation must.

According to this embodiment, the cellulose present in the biomass is converted to glucose, and at the same time, in the same reactor, the fermentative organism (for example a yeast) converts the glucose to the final product according to an SSF (Simultaneous Saccharification and Fermentation) process known to those skilled in the art. Depending on the metabolic and hydrolytic capacities of the fermentative organism, it may be necessary to add a more or less significant amount of exogenous cellulolytic mixture in order for the operation to proceed correctly.

In another embodiment, the fermentative organism produces the polypeptide which is the subject matter of the invention by secretion or at the surface of its cell, optionally together with other enzymes which act on lignocellulosic biomass, thus limiting or eliminating the need for enzymes produced by the filamentous fungus. Preferably, the fermentative organism is a host cell as described above.

Preferably, the host cells with the enzymatic composition and/or the fermentative organism are added and then incubated at a temperature of between 30° C. and 35° C. so as to produce a fermentation must.

The use of the polypeptide having a better exoglucanase activity according to the present invention thus has the advantage of obtaining a better glucose production yield while at the same time using less enzyme than previously, thereby also having an economic advantage.

Other aspects, subjects, advantages and features of the invention will be presented on reading the non-restrictive description which follows and which describes preferred embodiments of the invention, given by means of examples and of the FIGURES.

FIG. 1 is a MALDI-TOF mass spectrum representing the DP3 to DP11 cellodextrins used for the screening.

EXAMPLES

Example 1: Preparation Reduced Cellodextrins (DP 3-11)

1—Cellulose Hydrolysis
(Adapted from Y-H. Percival Zhang, L. R. Lynd Analytical Biochemistry 322 (2003), 225-232.)

20 g of cellulose (Avicel, CAS Number 9004-34-6, Sigma-Aldrich Saint-Quentin Fallavier) are added portionwise and with vigorous stirring to 160 ml of a hydrochloric acid solution cooled to 0° C. Precooled sulfuric acid is added to the solution in several steps (4×10 ml). The reaction is kept stirring for four hours at 24° C. before being poured into 1.8 l of acetone cooled to −20° C. After two hours of stirring, the precipitate is filtered off, taken up in 400 ml of cooled acetone and then again filtered. The solid is then taken up in 600 ml of water, and then stirred overnight in order to dissolve the cellodextrins (CDs). After the solid has been filtered off, the soluble fraction containing the cellodextrins is neutralized with 300 g of Amberlite IRA 400 OH⁻ resin and then lyophilized. The lyophilisate is then resuspended in 500 ml of methanol in the presence of ultrasound for 30 minutes in order to dissolve the low-molecular-weight sugars, before being filtered and then lyophilized again so as to give 6.8 g of DP 3-11 cellodextrins.

For the screening, it was chosen to work with substrates of the highest possible molecular weight in order to mimic as closely as possible the structure of cellulose. However, high-molecular-weight cellodextrins are not soluble, which prevents good reproducibility of the tests.

A range of cellodextrins of DP 5-7 was therefore chosen, which represents a good compromise between the high molecular weight required and the solubility of the cellodextrins.

FIG. 1 presents a MALDI-TOF mass spectrum typically obtained according to the process described above.

FIG. 1 shows that the isolated oligosaccharides are predominantly of DP 5-7.

2—Cellodextrin Reduction 400 mg of sodium borohydride are added to 2 g of DP 3-11 cellodextrins diluted in 120 ml of water. After three hours with stirring at ambient temperature, the solution is neutralized by adding Amberlite H⁺ IR 120 resin, filtered, and then lyophilized, so as to give 2 g of quantitatively reduced cellodextrins (C. Schou, G. Rasmussen, M-B. Kaltoft, B. Henrissat, M. Schulein Eur. J. Biochem. 217, 947-953 (1993)).

Assaying of the isolated cellodextrins with BCA (bicinchoninic acid) makes it possible to verify the total reduction of the ends (Y.-H. Percival Zhang, L. R. Lynd Biomacromolecules 2005, 6, 1510-1515).

Example 2: Evolution by L-Shuffling

The sequence of the cellobiohydrolase 2 gene from *Trichoderma reesei* (SEQ ID NO: 1) was subjected to a round of L-shuffling according to the patented process described in patent EP 1 104 457 with the genes of a putative exoglucanase from *Giberella zeae* PH-1 (SEQ ID NO: 29) and of a hypothetical protein NECHADRAFT 73991 from *Nectria haematococca* mpVI (SEQ ID NO: 31) having respectively 63% and 69% homology with the parental gene CBH2 (SEQ ID NO: 1). The nucleic sequence encoding the signal peptide (SEQ ID NO: 33) was deleted during the cloning, and replaced with that of yeast, of sequence SEQ ID NO: 34 (sequence of the corresponding signal peptide: SEQ ID NO: 35).

1—High-Throughput Screening

A high-throughput screening test was developed in order to select the best clones resulting from the L-shuffling, i.e. those exhibiting at least 20% improvement in the cellobiohydrolase activity compared with the CBH2 reference enzyme (SEQ ID NO: 2).

The high-throughput screening test was carried out according to the following steps:
isolation on agar of the clones of *Y. lipolytica* expressing the L-shuffling variants of the enzyme according to the invention and preculturing in YNB casa medium (yeast nitrogen base 1.7 g/l, NH₄Cl 10 g/l, glucose 10 g/l, casamino acids 2 g/l, pH 7) of said colonies for 36 hours at 28° C.;

inoculation of a YTD medium (yeast extract 10 g/l, tryptone 20 g/l, glucose 2.5 g/l, pH 6.8) supplemented with tetracycline at 12.5 μg/ml at 5% with the preculture and then incubation for 20 hours at 28° C.;

inoculation of the expression medium containing the inducer (oleic acid) in an amount of 20 g/l at 10% with the previous culture and then incubation for 96 hours at 28° C.;

centrifugation for five minutes at 1500 rpm;

removal of 100 μl of supernatant;

addition of 100 μl of reduced CDs at 1 g/l in 0.1 M citrate phosphate buffer at pH 6;

incubation for 24 hours at 35° C.;

centrifugation for five minutes at 2500 rpm;

removal of 80 μl of supernatant;

addition of 80 μl of DNS reagent;

incubation for 12 minutes at 105° C. and then five minutes on ice;

reading of the optical density (OD) at 540 nm on 120 μl.

Under these screening conditions, an improvement in the cellobiohydrolase activity (increase in the OD at 540 nm) compared with the CBH2 reference enzyme (SEQ ID NO: 2) was found in several clones. Among these clones, mention may be made of the 35B7, 95B7, 100F11, 139F12, 157B11, 161A1, 161C12, 189H8, 196D9, 198E11, 251B4, 251C4 and 382A2, encoding respectively the enzymes SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26 and SEQ ID NO: 28.

2—Determination of the Improvement in the Cellobiohydrolase Activity 2-1/ On the Reduced-Cellodextrin Substrate In order to estimate the relative kcat of the variants selected in the first round of L-shuffling with respect to the CBH2 reference enzyme (SEQ ID NO: 2), the following process is carried out:

preparation of a stock culture of *Y. lipolytica* expressing a recombinant enzyme according to the invention, overnight at 28° C.;

inoculation of an expression medium with a volume of stock culture making it possible to have an optical density at 600 nm equal to 0.2 at the beginning of the culture;

culture of said cells at 28° C. for 96 hours;

centrifugation at 8000 rpm for five minutes;

incubation of 100 μl of supernatant with 100 μl of 0.1 M citrate phosphate buffer, pH 6, containing 1% of reduced CDs, for 4 hours at 35° C. and 50° C.;

removal of 100 μl of reaction;

addition of 100 μl of DNS reagent;

incubation for five minutes at 100° C.;

incubation for three minutes on ice;

centrifugation for 10 minutes at 3000 rpm;

reading of the optical density at 540 nm on 150 μl.

According to the invention, the calculation of the kcats is carried out in the following way:

plotting the curve of the ODs at 540 nm as a function of the volume of culture supernatant in the test;

subtracting the value of the negative control;

dividing by the coefficient of the glucose standard rate (various amounts of glucose are revealed with the DNS);

dividing by the reaction time (240 minutes).

Table 2 gives the value of the kcats and also the improvement factor obtained for the 35B7, 95B7, 100F11, 139F12, 157B11, 161A1, 161C12, 189H8, 196D9, 198E11, 251B4, 251C4 and 382A2 clones encoding respectively the enzymes SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26 and SEQ ID NO: 28 compared with the CBH2 reference protein (SEQ ID NO: 2) under these experimental conditions.

TABLE 2 improvement in the cellobiohydrolase activity on reduced CDs

| | | 35° C. | | 50° C. | |
|---|---|---|---|---|---|
| | Clone | Kcat (min$^{-1}$) | Improvement factor | Kcat (min$^{-1}$) | Improvement factor |
| First-round clones | 35B7 | 0.166 | 3.8 | 0.2345 | 1.6 |
| | 95B7 | 0.287 | 6.6 | 0.715 | 4.8 |
| | 100F11 | 0.0508 | 1.2 | 0.1375 | 0.9 |
| | 139F12 | 0.1719 | 3.9 | 0.2328 | 1.6 |
| | 157B11 | 0.113 | 2.6 | 0.2061 | 1.4 |
| | 161A1 | 0.0577 | 1.3 | 0.1175 | 0.8 |
| | 161C12 | 0.1086 | 2.5 | 0.2162 | 1.4 |
| | 189H8 | 0.0872 | 2.0 | 0.1792 | 1.2 |
| | 196D9 | 0.1055 | 2.4 | 0.1969 | 1.3 |
| | 198E11 | 0.1218 | 2.8 | 0.1757 | 1.2 |
| | 251B4 | 0.0495 | 1.1 | 0.0865 | 0.6 |
| | 251C4 | 0.0623 | 1.4 | 0.1315 | 0.9 |
| | 382A2 | 0.315 | 7.2 | 0.552 | 3.7 |
| Reference protein | cbh2 | 0.0436 | 1 | 0.1501 | 1 |

The results show an improvement in enzymatic activity compared with the CBH2 reference enzyme (SEQ ID NO: 2) for the 35B7, 95B7, 100F11, 139F12, 157B11, 161A1, 161C12, 189H8, 196D9, 198E11, 251B4, 251C4 and 382A2 clones encoding respectively the enzymes SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26 and SEQ ID NO: 28, whether at 35° C. or at 50° C.

2-2/ On the Avicel Substrate

The improvement in activity of the 35B7, 95B7, 100F11, 139F12, 157B11, 161A1, 161C12, 189H8, 196D9, 198E11, 251B4, 251C4 and 382A2 clones encoding respectively the enzymes SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26 and SEQ ID NO: 28 was then measured with a second substrate: Avicel.

The determination of the improvement in the activity on this substrate is carried out by end-point measurement according to the following protocol:

preparation of a stock culture of *Y. lipolytica* expressing a recombinant enzyme according to the invention, overnight at 28° C.;

inoculation of an expression medium with a volume of stock culture making it possible to have an optical density at 600 nm equal to 0.2 at the beginning of the culture;

culture of said cells at 28° C. for 96 hours;

centrifugation at 8000 rpm for 5 minutes;

incubation of 100 μl of supernatant with 100 μl of 0.1 M citrate phosphate buffer, pH 6, containing 1% of Avicel, for 18 hours at 35 and 50° C.;

removal of 100 μl of reaction;

addition of 100 μl of DNS reagent;

incubation for 5 minutes at 100° C.;

incubation for 3 minutes on ice;

centrifugation for 10 minutes at 3000 rpm;
reading the optical density at 540 nm on 150 μl.

Table 3 presents the value of the ODs at 540 nm (after subtraction of the value of the negative control) and also the improvement factor obtained for the 35B7, 95B7, 100F11, 139F12, 157B11, 161A1, 161C12, 189H8, 196D9, 198E11, 251B4, 251C4 and 382A2 clones under these experimental conditions.

TABLE 3 improvement in the cellobiohydrolase activity on Avicel

| | | 35° C. | | 50° C. | |
|---|---|---|---|---|---|
| | Clone | Delta OD 540 nm | Improvement factor | Delta OD 540 nm | Improvement factor |
| First-round clones | 35B7 | 0.0617 | 1.0 | 0.0948 | 0.8 |
| | 95B7 | 0.0396 | 0.6 | 0.0555 | 0.4 |
| | 100F11 | 0.038 | 0.6 | 0.0159 | 0.1 |
| | 139F12 | 0.06 | 0.9 | 0.0365 | 0.3 |
| | 157B11 | 0.0456 | 0.7 | 0.0319 | 0.3 |
| | 161A1 | 0.0508 | 0.8 | 0.0237 | 0.2 |
| | 161C12 | 0.0564 | 0.9 | 0.0595 | 0.5 |

TABLE 3-continued improvement in the cellobiohydrolase activity on Avicel

| | | 35° C. | | 50° C. | |
|---|---|---|---|---|---|
| | Clone | Delta OD 540 nm | Improvement factor | Delta OD 540 nm | Improvement factor |
| | 189H8 | 0.0676 | 1.0 | 0.0573 | 0.5 |
| | 196D9 | 0.0565 | 0.9 | 0.0874 | 0.7 |
| | 198E11 | 0.0867 | 1.3 | 0.0546 | 0.4 |
| | 251B4 | 0.0765 | 1.2 | 0.0622 | 0.5 |
| | 251C4 | 0.063 | 1.0 | 0.0889 | 0.7 |
| | 382A2 | 0.2476 | 3.8 | 0.2256 | 1.8 |
| Reference protein | cbh2 | 0.0644 | 1 | 0.1252 | 1 |

The results from table 3 show an improvement in the enzymatic activity, compared with the CBH2 reference enzyme (SEQ ID NO: 2) at 35° C. for the 198E11 and 251B4 clones (respectively SEQ ID Nos: 22 and 24) and also an improvement in the enzymatic activity compared with the CBH2 reference enzyme (SEQ ID NO: 2) at 35° C. and at 50° C. for the 382A2 clone (SEQ ID NO: 28).

The invention claimed is:

1. An isolated or purified polypeptide having an improved exoglucanase activity of at least 10% at a temperature of 35° C. compared with the exoglucanase activity of the exoglucanase 2 reference protein of SEQ ID NO: 2,
said polypeptide being selected from the group consisting of:
  i. the amino acid sequence selected from SEQ ID NO: 22, SEQ ID NO: 24, and SEQ ID NO: 28; and
  ii. an amino acid sequence having a percentage identity of at least 98% compared with the sequence SEQ ID NO: 22, SEQ ID NO: 24, and SEQ ID NO: 28.

2. An enzymatic composition capable of acting on lignocellulosic biomass, said enzymatic composition being produced by filamentous fungi and comprising at least one polypeptide as claimed in claim 1.

3. An isolated or purified polypeptide according to claim 1,
said polypeptide being selected from the group consisting of: an amino acid sequence having a percentage identity of at least 99% compared with the sequence SEQ ID NO: 22, SEQ ID NO: 24, and SEQ ID NO: 28.

4. A process for producing biofuel from lignocellulosic biomass, comprising the following successive steps:

the biomass to be hydrolyzed is suspended in an aqueous phase;
the lignocellulosic biomass is hydrolyzed in the presence of an enzymatic composition comprising at least one polypeptide as claimed in claim 1 the biomass so as to produce a hydrolysate containing glucose;
the glucose of the hydrolysate is fermented in the presence of a fermentative organism so as to produce a fermentation must;
the biofuel is separated from the fermentation must.

5. A process for producing biofuel from biomass, comprising the following successive steps:
the biomass to be hydrolyzed is suspended in an aqueous phase;
an enzymatic composition comprising at least one polypeptide as claimed in claim 1 and a fermentative organism are added simultaneously to the suspension and the mixture is fermented so as to produce a fermentation must;
the biofuel is separated from the fermentation must.

6. A process for hydrolyzing cellulosis comprising the use of a polypeptide according to claim 1.

7. A process for producing biofuel comprising the use of a polypeptide according to claim 1.

* * * * *

SEQUENCE LISTING

<160> NUMBER OF SEQ ID NOS: 35

<210> SEQ ID NO 1
<211> LENGTH: 1413
<212> TYPE: DNA
<213> ORGANISM: Trichoderma reesei

<400> SEQUENCE: 1

```
atgattgtcg gcattctcac cacgctggct acgctggcca cactcgcagc tagtgtgcct      60
ctagaggagc ggcaagcttg ctcaagcgtc tggggccaat gtggtggcca gaattggtcg     120
ggtccgactt gctgtgcttc cggaagcaca tgcgtctact ccaacgacta ttactcccag     180
tgtcttcccg gcgctgcaag ctcaagctcg tccacgcgcg ccgcgtcgac gacttctcga     240
gtatccccca caacatcccg gtcgagctcc gcgacgcctc cacctggttc tactactacc     300
agagtacctc cagtcggatc gggaaccgct acgtattcag gcaaccctt tgttggggtc     360 actccttggg ccaatgcata ttacgcctct gaagttagca gcctcgctat tcctagcttg     420
actggagcca tggccactgc tgcagcagct gtcgcaaagg ttccctcttt tatgtggcta     480
gatactcttg acaagacccc tctcatggag caaaccttgg ccgacatccg caccgccaac     540
aagaatggcg gtaactatgc cggacagttt gtggtgtatg acttgccgga tcgcgattgc     600
gctgcccttg cctcgaatgg cgaatactct attgccgatg gtggcgtcgc caaatataag     660
aactatatcg acaccattcg tcaaattgtc gtggaatatt ccgatatccg gaccctcctg     720
gttattgagc ctgactctct tgccaacctg gtgaccaacc tcggtactcc aaagtgtgcc     780
aatgctcagt cagcctacct tgagtgcatc aactacgccg tcacacagct gaaccttcca     840
aatgttgcga tgtatttgga cgctggccat gcaggatggc ttggctggcc ggcaaaccaa     900
gacccggccg ctcagctatt tgcaaatgtt tacaagaatg catcgtctcc gagagctctt     960
cgcggattgg caaccaatgt cgccaactac aacgggtgga acattaccag cccccatcg    1020 tacacgcaag gcaacgctgt ctacaacgag aagctgtaca tccacgctat ggacctctt    1080 cttgccaatc acgctggtc caacgccttc ttcatcactg atcaaggtcg atcggaaag    1140 cagcctaccg gacagcaaca gtggggagac tggtgcaatg tgatcggcac cggatttggt    1200
```

-continued

```
attcgcccat ccgcaaacac tggggactcg ttgctggatt cgtttgtctg ggtcaagcca      1260
ggcggcgagt gtgacggcac cagcgacagc agtgcgccac gatttgactc ccactgtgcg      1320
ctcccagatg ccttgcaacc ggcgcctcaa gctggtgctt ggttccaagc ctactttgtg      1380
cagcttctca caaacgcaaa cccatcgttc ctg                                    1413

<210> SEQ ID NO 2
<211> LENGTH: 471
<212> TYPE: PRT
<213> ORGANISM: Trichoderma reesei

<400> SEQUENCE: 2

Met Ile Val Gly Ile Leu Thr Thr Leu Ala Thr Leu Ala Thr Leu Ala
1               5                   10                  15

Ala Ser Val Pro Leu Glu Glu Arg Gln Ala Cys Ser Ser Val Trp Gly
                20                  25                  30

Gln Cys Gly Gly Gln Asn Trp Ser Gly Pro Thr Cys Cys Ala Ser Gly
            35                  40                  45

Ser Thr Cys Val Tyr Ser Asn Asp Tyr Tyr Ser Gln Cys Leu Pro Gly
        50                  55                  60

Ala Ala Ser Ser Ser Ser Ser Thr Arg Ala Ala Ser Thr Thr Ser Arg
65                  70                  75                  80

Val Ser Pro Thr Thr Ser Arg Ser Ser Ala Thr Pro Pro Pro Gly
                85                  90                  95

Ser Thr Thr Thr Arg Val Pro Pro Val Gly Ser Gly Thr Ala Thr Tyr
                100                 105                 110

Ser Gly Asn Pro Phe Val Gly Val Thr Pro Trp Ala Asn Ala Tyr Tyr
            115                 120                 125

Ala Ser Glu Val Ser Ser Leu Ala Ile Pro Ser Leu Thr Gly Ala Met
        130                 135                 140

Ala Thr Ala Ala Ala Val Ala Lys Val Pro Ser Phe Met Trp Leu
145                 150                 155                 160

Asp Thr Leu Asp Lys Thr Pro Leu Met Glu Gln Thr Leu Ala Asp Ile
                165                 170                 175

Arg Thr Ala Asn Lys Asn Gly Gly Asn Tyr Ala Gly Gln Phe Val Val
            180                 185                 190

Tyr Asp Leu Pro Asp Arg Asp Cys Ala Ala Leu Ala Ser Asn Gly Glu
        195                 200                 205

Tyr Ser Ile Ala Asp Gly Gly Val Ala Lys Tyr Lys Asn Tyr Ile Asp
    210                 215                 220

Thr Ile Arg Gln Ile Val Val Glu Tyr Ser Asp Ile Arg Thr Leu Leu
225                 230                 235                 240

Val Ile Glu Pro Asp Ser Leu Ala Asn Leu Val Thr Asn Leu Gly Thr
                245                 250                 255

Pro Lys Cys Ala Asn Ala Gln Ser Ala Tyr Leu Glu Cys Ile Asn Tyr
            260                 265                 270

Ala Val Thr Gln Leu Asn Leu Pro Asn Val Ala Met Tyr Leu Asp Ala
        275                 280                 285

Gly His Ala Gly Trp Leu Gly Trp Pro Ala Asn Gln Asp Pro Ala Ala
    290                 295                 300

Gln Leu Phe Ala Asn Val Tyr Lys Asn Ala Ser Ser Pro Arg Ala Leu
305                 310                 315                 320

Arg Gly Leu Ala Thr Asn Val Ala Asn Tyr Asn Gly Trp Asn Ile Thr
                325                 330                 335
```

```
Ser Pro Pro Ser Tyr Thr Gln Gly Asn Ala Val Tyr Asn Glu Lys Leu
            340                 345                 350

Tyr Ile His Ala Ile Gly Pro Leu Leu Ala Asn His Gly Trp Ser Asn
            355                 360                 365

Ala Phe Phe Ile Thr Asp Gln Gly Arg Ser Gly Lys Gln Pro Thr Gly
370                 375                 380

Gln Gln Gln Trp Gly Asp Trp Cys Asn Val Ile Gly Thr Gly Phe Gly
385                 390                 395                 400

Ile Arg Pro Ser Ala Asn Thr Gly Asp Ser Leu Leu Asp Ser Phe Val
                405                 410                 415

Trp Val Lys Pro Gly Gly Glu Cys Asp Gly Thr Ser Asp Ser Ser Ala
                420                 425                 430

Pro Arg Phe Asp Ser His Cys Ala Leu Pro Asp Ala Leu Gln Pro Ala
                435                 440                 445

Pro Gln Ala Gly Ala Trp Phe Gln Ala Tyr Phe Val Gln Leu Leu Thr
            450                 455                 460

Asn Ala Asn Pro Ser Phe Leu
465                 470

<210> SEQ ID NO 3
<211> LENGTH: 1353
<212> TYPE: DNA
<213> ORGANISM: Artificial Sequence
<220> FEATURE:
<223> OTHER INFORMATION: Clone 35B7

<400> SEQUENCE: 3
gcccctcttg ttgaggagcg ccaggcttgc gctgcccaat gggcccagtg tggtggcttc      60
agctggaatg gtgctacctg ctgccagtct ggtagctact gcagcaagat caacgactat     120
tactctcagt gcattcctgg agaaggcccc gccacttcca gtcgagcac tcttcctgct      180 tccaccacaa caactcagcc aacttccact tcgactgctg aacctcttc cactaccaag      240 cctcctccag ctggatcggg aaccgctacg tattcaggca acccttactc tggggtcaac     300
ctttgggcca atagctatta ccgctctgaa gttaccaacc tcgctattcc taagttgagc     360
ggagccatgg ccactgctgc agcaaaggtc gcagatgttc cctcttttca gtggatggat     420
tctttcgacc acatctccct catggaggac accttggtcg acatccgcaa ggccaacctg     480
gctggcggta actatgccgg acagtttgtg gtgtatgact tgccggatcg cgattgcgct     540
gccgccgcct cgaatggcga atactctctt gccgatggtg gcgtcgccaa atataaggcc     600
tatatcgcca agattaaggg tattctccag gactattccg ataccggat cattctggtt     660 attgagcctg actctcttgc caacctggtg accaacatga acgtcccaaa gtgtgccaat     720
gctgcttcag cctacaagga gctcaccatt cacgccctca aggagctgaa ccttccaaat     780
gtttccatgt atatcgacgc tggccatggt ggatggcttg ctggccggc aaaccaaggc     840 ccggccgcta actatttgc aagcatctac aaggatgcag gcaagccggc cgctcttcgc     900
ggattggcaa ccaatgtcgc caactacaac gcctggagcc tcagcagcgc tccaccttac     960
acgcaaggcg cctctatcta cgacgagaag agcttcatcc acgctatggg acctcttctt    1020
gagcagaatg gctggcctgg tgcccacttc atcactgatc aaggtcgatc gggaaagcag    1080
cctaccggac agatccagtg gggagactgg tgcaattcca agggcaccgg atttggtatt    1140
cgcccatccg caaacactgg ggactcgttg ctggatgctt ttgtctgggt caagccaggc    1200
ggcgagtctg acggcaccag cgacaccagt gcggctcgat acgactacca ctgtggtatt    1260
```

```
gacggcgccg tcaagccggc gcctgaggct ggtacctggt tccaagccta ctttgagcag    1320
cttctcacaa acgcaaaccc atcgttcctg taa                                 1353
```

<210> SEQ ID NO 4
<211> LENGTH: 450
<212> TYPE: PRT
<213> ORGANISM: Artificial Sequence
<220> FEATURE:
<223> OTHER INFORMATION: Clone 35B7

<400> SEQUENCE: 4

```
Ala Pro Leu Val Glu Glu Arg Gln Ala Cys Ala Ala Gln Trp Ala Gln
1               5                   10                  15

Cys Gly Gly Phe Ser Trp Asn Gly Ala Thr Cys Cys Gln Ser Gly Ser
            20                  25                  30

Tyr Cys Ser Lys Ile Asn Asp Tyr Tyr Ser Gln Cys Ile Pro Gly Glu
        35                  40                  45

Gly Pro Ala Thr Ser Lys Ser Ser Thr Leu Pro Ala Ser Thr Thr Thr
    50                  55                  60

Thr Gln Pro Thr Ser Thr Ser Thr Ala Gly Thr Ser Ser Thr Thr Lys
65                  70                  75                  80

Pro Pro Pro Ala Gly Ser Gly Thr Ala Thr Tyr Ser Gly Asn Pro Tyr
                85                  90                  95

Ser Gly Val Asn Leu Trp Ala Asn Ser Tyr Tyr Arg Ser Glu Val Thr
            100                 105                 110

Asn Leu Ala Ile Pro Lys Leu Ser Gly Ala Met Ala Thr Ala Ala Ala
        115                 120                 125

Lys Val Ala Asp Val Pro Ser Phe Gln Trp Met Asp Ser Phe Asp His
    130                 135                 140

Ile Ser Leu Met Glu Asp Thr Leu Val Asp Ile Arg Lys Ala Asn Leu
145                 150                 155                 160

Ala Gly Gly Asn Tyr Ala Gly Gln Phe Val Val Tyr Asp Leu Pro Asp
                165                 170                 175

Arg Asp Cys Ala Ala Ala Ala Ser Asn Gly Glu Tyr Ser Leu Ala Asp
            180                 185                 190

Gly Gly Val Ala Lys Tyr Lys Ala Tyr Ile Ala Lys Ile Lys Gly Ile
        195                 200                 205

Leu Gln Asp Tyr Ser Asp Thr Arg Ile Ile Leu Val Ile Glu Pro Asp
    210                 215                 220

Ser Leu Ala Asn Leu Val Thr Asn Met Asn Val Pro Lys Cys Ala Asn
225                 230                 235                 240

Ala Ala Ser Ala Tyr Lys Glu Leu Thr Ile His Ala Leu Lys Glu Leu
                245                 250                 255

Asn Leu Pro Asn Val Ser Met Tyr Ile Asp Ala Gly His Gly Gly Trp
            260                 265                 270

Leu Gly Trp Pro Ala Asn Gln Gly Pro Ala Ala Lys Leu Phe Ala Ser
        275                 280                 285

Ile Tyr Lys Asp Ala Gly Lys Pro Ala Ala Leu Arg Gly Leu Ala Thr
    290                 295                 300

Asn Val Ala Asn Tyr Asn Ala Trp Ser Leu Ser Ala Pro Pro Tyr
305                 310                 315                 320

Thr Gln Gly Ala Ser Ile Tyr Asp Glu Lys Ser Phe Ile His Ala Met
                325                 330                 335

Gly Pro Leu Leu Glu Gln Asn Gly Trp Pro Gly Ala His Phe Ile Thr
```

340                 345                 350
Asp Gln Gly Arg Ser Gly Lys Gln Pro Thr Gly Gln Ile Gln Trp Gly
            355                 360                 365

Asp Trp Cys Asn Ser Lys Gly Thr Gly Phe Gly Ile Arg Pro Ser Ala
        370                 375                 380

Asn Thr Gly Asp Ser Leu Leu Asp Ala Phe Val Trp Val Lys Pro Gly
385                 390                 395                 400

Gly Glu Ser Asp Gly Thr Ser Asp Thr Ser Ala Ala Arg Tyr Asp Tyr
                405                 410                 415

His Cys Gly Ile Asp Gly Ala Val Lys Pro Ala Pro Glu Ala Gly Thr
            420                 425                 430

Trp Phe Gln Ala Tyr Phe Glu Gln Leu Leu Thr Asn Ala Asn Pro Ser
        435                 440                 445

Phe Leu
    450

<210> SEQ ID NO 5
<211> LENGTH: 1362
<212> TYPE: DNA
<213> ORGANISM: Artificial Sequence
<220> FEATURE:
<223> OTHER INFORMATION: Clone 95B7

<400> SEQUENCE: 5

```
gtgcctctag aggagcggca agcttgctca agcgtctggg gccaatgtgg tggccagaat      60
tggtcgggtc cgacttgctg tgcttccgga agcacatgcg tctactccaa cgactattac     120
tcccagtgtc ttcccggcgc tgcaagctca agctcgtcca cgcgcgccgc gtcgacgact     180
tctcgagtat cccccacaac atcccggtcg agctccgcga cgcctccacc tggttctact     240
actaccagag tacctccagt cggatcggga accgctacgt attcaggcaa ccctttttgtt     300
ggggtcactc cttgggccaa tgcatattac gcctctgaag ttagcagcct cgctattcct     360
agcttgactg gagccatggc cactgctgca gcagctgtcg caaaggttcc ctcttttatg     420
tggctagata ctcttgacaa gaccccctctc atggagcaaa ccttggccga catccgcacc     480
gccaacaaga atggcggtaa ctatgccgga cagtttgtgg tgtatgactt gccggatcgc     540
gattgcgctg cccttgcctc gaatggcgaa tactctattg ccgatggtgg cgtcgccaaa     600
tataagaact atatcgacac cattcgtcaa attgtcgtgg aatattccga tatccggacc     660
ctcctggtta ttgagcctga ctctcttgcc aaccaggtga ccaacatgga tgtcgccaag     720
tgtgccaagg tcatgatgc ctacatcagc ctgacgaact acgccgtcac agaactgaac     780
cttccaaatg ttgcgatgta tttggacgct ggcaatgcag gatggcttgg ctggccggca     840
aaccaaggcc cggccgctaa actatttgca agcatctaca aggatgcagg caagccggcc     900
gctcttcgcg gattggcaac caatgtcgcc aactacaacg cctggagcct cagcagcgct     960
ccaccttaca cgcaaggcgc ctctatctac gacgagaaga gcttcatcca cgctatggga    1020
cctcttcttg agcagaatgg ctggcctggt gcccacttca tcactgatca aggtcgatcg    1080
ggaaagcagc ctaccggaca gatccagtgg ggagactggt gcaattccaa gggcaccgga    1140
tttggtattc gcccatccgc aaacactggg gactcgttgc tggatgcttt tgtctgggtc    1200
aagccaggcg gcgagtctga cggcaccagc gacaccagtg cgacccgata cgactaccac    1260
tgtggtgctt ctgccgcctt gcaaccggcc cctgaggctg gtacctggtt ccaagcctac    1320
tttgagcagc ttctcaagaa cgcaaaccca tcgttcctgt aa                       1362
```

-continued

<210> SEQ ID NO 6
<211> LENGTH: 453
<212> TYPE: PRT
<213> ORGANISM: Artificial Sequence
<220> FEATURE:
<223> OTHER INFORMATION: Clone 95B7

<400> SEQUENCE: 6

```
Val Pro Leu Glu Glu Arg Gln Ala Cys Ser Ser Val Trp Gly Gln Cys
1               5                   10                  15

Gly Gly Gln Asn Trp Ser Gly Pro Thr Cys Cys Ala Ser Gly Ser Thr
            20                  25                  30

Cys Val Tyr Ser Asn Asp Tyr Tyr Ser Gln Cys Leu Pro Gly Ala Ala
        35                  40                  45

Ser Ser Ser Ser Ser Thr Arg Ala Ala Ser Thr Thr Ser Arg Val Ser
    50                  55                  60

Pro Thr Thr Ser Arg Ser Ser Ala Thr Pro Pro Gly Ser Thr
65                  70                  75                  80

Thr Thr Arg Val Pro Pro Val Gly Ser Gly Thr Ala Thr Tyr Ser Gly
                85                  90                  95

Asn Pro Phe Val Gly Val Thr Pro Trp Ala Asn Ala Tyr Tyr Ala Ser
            100                 105                 110

Glu Val Ser Ser Leu Ala Ile Pro Ser Leu Thr Gly Ala Met Ala Thr
        115                 120                 125

Ala Ala Ala Ala Val Ala Lys Val Pro Ser Phe Met Trp Leu Asp Thr
    130                 135                 140

Leu Asp Lys Thr Pro Leu Met Glu Gln Thr Leu Ala Asp Ile Arg Thr
145                 150                 155                 160

Ala Asn Lys Asn Gly Gly Asn Tyr Ala Gly Gln Phe Val Val Tyr Asp
                165                 170                 175

Leu Pro Asp Arg Asp Cys Ala Ala Leu Ala Ser Asn Gly Glu Tyr Ser
            180                 185                 190

Ile Ala Asp Gly Gly Val Ala Lys Tyr Lys Asn Tyr Ile Asp Thr Ile
        195                 200                 205

Arg Gln Ile Val Val Glu Tyr Ser Asp Ile Arg Thr Leu Leu Val Ile
    210                 215                 220

Glu Pro Asp Ser Leu Ala Asn Gln Val Thr Asn Met Asp Val Ala Lys
225                 230                 235                 240

Cys Ala Lys Ala His Asp Ala Tyr Ile Ser Leu Thr Asn Tyr Ala Val
                245                 250                 255

Thr Glu Leu Asn Leu Pro Asn Val Ala Met Tyr Leu Asp Ala Gly Asn
            260                 265                 270

Ala Gly Trp Leu Gly Trp Pro Ala Asn Gln Gly Pro Ala Ala Lys Leu
        275                 280                 285

Phe Ala Ser Ile Tyr Lys Asp Ala Gly Lys Pro Ala Ala Leu Arg Gly
    290                 295                 300

Leu Ala Thr Asn Val Ala Asn Tyr Asn Ala Trp Ser Leu Ser Ser Ala
305                 310                 315                 320

Pro Pro Tyr Thr Gln Gly Ala Ser Ile Tyr Asp Glu Lys Ser Phe Ile
                325                 330                 335

His Ala Met Gly Pro Leu Leu Glu Gln Asn Gly Trp Pro Gly Ala His
            340                 345                 350

Phe Ile Thr Asp Gln Gly Arg Ser Gly Lys Gln Pro Thr Gly Gln Ile
        355                 360                 365
```

```
Gln Trp Gly Asp Trp Cys Asn Ser Lys Gly Thr Gly Phe Gly Ile Arg
    370                 375                 380

Pro Ser Ala Asn Thr Gly Asp Ser Leu Leu Asp Ala Phe Val Trp Val
385                 390                 395                 400

Lys Pro Gly Gly Glu Ser Asp Gly Thr Ser Asp Thr Ser Ala Thr Arg
                405                 410                 415

Tyr Asp Tyr His Cys Gly Ala Ser Ala Ala Leu Gln Pro Ala Pro Glu
                420                 425                 430

Ala Gly Thr Trp Phe Gln Ala Tyr Phe Glu Gln Leu Leu Lys Asn Ala
            435                 440                 445

Asn Pro Ser Phe Leu
    450

<210> SEQ ID NO 7
<211> LENGTH: 1323
<212> TYPE: DNA
<213> ORGANISM: Artificial Sequence
<220> FEATURE:
<223> OTHER INFORMATION: Clone 100F11

<400> SEQUENCE: 7
gctcctgttg aagagcgtca gtcttgcagc aacggagtct ggtctcaatg tggtggtcag      60
aactggtccg gtactccttg ctgcaccagt ggaaacaagt gtgtcaaggt caacgacttc     120
tactcccagt gccagcctgg atctgcagac ccttctccca catccaccat tgtctccgcg     180
acgaccacca aggctactac tactggtagt ggaggctctg tcacctcgcc tcctcctgtt     240
gccaccaaca ccctttttc tggggtcgat ctgtgggcca ataactatta ccgctctgaa     300
gttagcactc tcgctattcc taagttgagc ggagccatgg ccactgctgc agcaaaggtc     360
gcagatgttc cctcttttca gtggatggat acttatgacc acatctcctt catggaggag     420
tctttggccg acatccgcaa ggccaacaag gctggcggta actatgccgg acagtttgtg     480
gtgtatgact gccggatcg cgattgcgct gccgctgcct cgaatggcga atactctctt     540
gacaaggatg gcaagaacaa atataaggcc tatatcgcca agattaaggg tattctccag     600
gactattccg ataccggat cattctggtt attgagcctg actctcttgc aacatggtg     660 accaacatga acgtcccaaa gtgtgccaat gctgcttcag cctacaagga gctcaccatt     720
cacgccctca aggagctgaa ccttccaaat gtttccatgt atatcgacgc tggccatggt     780
ggatggcttg gctggccggc aaaccttcct ccggccgctc agctatacgg tcagctctac     840
aaggatgcag gcaagccgtc tcgccttcgc ggattggtca ccaatgtctc caactacaac     900
gcctggaagc tatccagcaa gccagactac acggagagca accccaacta cgacgagcag     960
aagtacatcc acgctctgtc tcctcttctt gagcaggagg gctggcccgg tgccaagttc    1020
atcgtcgatc aaggtcgatc gggaaagcag cctaccggac agaaggcttg gggagactgg    1080
tgcaatgctc ccggcaccgg atttggtatt cgcccatccg caaacactgg ggactcgttg    1140
ctggatgctt ttgtctgggt caagccaggc ggcgagtctg acggcaccag cgacaccagt    1200
gcgacccgat acgactacca ctgtggtgct tctgccgcct gcaaccggc gcctgaggct    1260 ggtacctggt tccaagccta ctttgagcag cttctcacaa acgcaaaccc atcgttcctg    1320
taa                                                                  1323

<210> SEQ ID NO 8
<211> LENGTH: 440
<212> TYPE: PRT
<213> ORGANISM: Artificial Sequence
```

<220> FEATURE:
<223> OTHER INFORMATION: Clone 100F11

<400> SEQUENCE: 8

```
Ala Pro Val Glu Glu Arg Gln Ser Cys Ser Asn Gly Val Trp Ser Gln
 1               5                  10                  15

Cys Gly Gly Gln Asn Trp Ser Gly Thr Pro Cys Cys Thr Ser Gly Asn
            20                  25                  30

Lys Cys Val Lys Val Asn Asp Phe Tyr Ser Gln Cys Gln Pro Gly Ser
        35                  40                  45

Ala Asp Pro Ser Pro Thr Ser Thr Ile Val Ser Ala Thr Thr Thr Lys
    50                  55                  60

Ala Thr Thr Thr Gly Ser Gly Gly Ser Val Thr Ser Pro Pro Pro Val
65                  70                  75                  80

Ala Thr Asn Asn Pro Phe Ser Gly Val Asp Leu Trp Ala Asn Asn Tyr
                85                  90                  95

Tyr Arg Ser Glu Val Ser Thr Leu Ala Ile Pro Lys Leu Ser Gly Ala
            100                 105                 110

Met Ala Thr Ala Ala Ala Lys Val Ala Asp Val Pro Ser Phe Gln Trp
        115                 120                 125

Met Asp Thr Tyr Asp His Ile Ser Phe Met Glu Glu Ser Leu Ala Asp
    130                 135                 140

Ile Arg Lys Ala Asn Lys Ala Gly Gly Asn Tyr Ala Gly Gln Phe Val
145                 150                 155                 160

Val Tyr Asp Leu Pro Asp Arg Asp Cys Ala Ala Ala Ser Asn Gly
                165                 170                 175

Glu Tyr Ser Leu Asp Lys Asp Gly Lys Asn Lys Tyr Lys Ala Tyr Ile
            180                 185                 190

Ala Lys Ile Lys Gly Ile Leu Gln Asp Tyr Ser Asp Thr Arg Ile Ile
        195                 200                 205

Leu Val Ile Glu Pro Asp Ser Leu Ala Asn Met Val Thr Asn Met Asn
    210                 215                 220

Val Pro Lys Cys Ala Asn Ala Ala Ser Ala Tyr Lys Glu Leu Thr Ile
225                 230                 235                 240

His Ala Leu Lys Glu Leu Asn Leu Pro Asn Val Ser Met Tyr Ile Asp
                245                 250                 255

Ala Gly His Gly Gly Trp Leu Gly Trp Pro Ala Asn Leu Pro Pro Ala
            260                 265                 270

Ala Gln Leu Tyr Gly Gln Leu Tyr Lys Asp Ala Gly Lys Pro Ser Arg
        275                 280                 285

Leu Arg Gly Leu Val Thr Asn Val Ser Asn Tyr Asn Ala Trp Lys Leu
    290                 295                 300

Ser Ser Lys Pro Asp Tyr Thr Glu Ser Asn Pro Asn Tyr Asp Glu Gln
305                 310                 315                 320

Lys Tyr Ile His Ala Leu Ser Pro Leu Leu Glu Gln Glu Gly Trp Pro
                325                 330                 335

Gly Ala Lys Phe Ile Val Asp Gln Gly Arg Ser Gly Lys Gln Pro Thr
            340                 345                 350

Gly Gln Lys Ala Trp Gly Asp Trp Cys Asn Ala Pro Gly Thr Gly Phe
        355                 360                 365

Gly Ile Arg Pro Ser Ala Asn Thr Gly Asp Ser Leu Leu Asp Ala Phe
    370                 375                 380

Val Trp Val Lys Pro Gly Gly Glu Ser Asp Gly Thr Ser Asp Thr Ser
385                 390                 395                 400
```

Ala Thr Arg Tyr Asp Tyr His Cys Gly Ala Ser Ala Ala Leu Gln Pro
            405                 410                 415

Ala Pro Glu Ala Gly Thr Trp Phe Gln Ala Tyr Phe Gln Leu Leu
        420                 425                 430

Thr Asn Ala Asn Pro Ser Phe Leu
        435                 440

<210> SEQ ID NO 9
<211> LENGTH: 1323
<212> TYPE: DNA
<213> ORGANISM: Artificial Sequence
<220> FEATURE:
<223> OTHER INFORMATION: Clone 139F12

<400> SEQUENCE: 9

```
gctcctgttg aagagcgtca gtcttgcagc aacggagtct ggtctcaatg tggtggtcag      60
aactggtccg gtactccttg ctgcaccagt ggaaacaagt gtgtcaaggt caacgacttc     120
tactcccagt gccagcctgg atctgcagac ccttctccca catccaccat tgtctccgcg     180
acgaccacca aggctactac tactggtagt ggaggctctg tcacctcgcc tcctcctgtt     240
gccaccaaca cccttttttc tggggtcgat ctgtgggcca ataactatta ccgctctgaa     300
gttagcactc tcgctattcc taagttgagc ggagccatgg ccactgctgc agcaaaggtc     360
gcagatgttc cctcttttca gtggatggat acttatgacc acatctcctt catggaggag     420
tctttggccg acatccgcaa ggccaacaag gctggcggta actatgccgg acagtttgtg     480
gtgtatgact gccggatcg cgattgcgct gccgctgcct cgaatggcga atactctctt     540
gacaaggatg gcaagaacaa atataaggcc tatatcgcca agattaaggg tattctccag     600
gactattccg atacccggat cattctggtt attgagcctg actctcttgc caacatggtg     660
accaacatga acgtcccaaa gtgtgccaat gctgcttcag cctacaagga gctcaccatt     720
cacgccctca aggagctgaa ccttccaaat gtttccatgt atatcgacgc tggccatggt     780
ggatggcttg gctggccggc aaaccttcct ccggccgctc agctatacgg tcagctctac     840
aaggatgcag gcaagccgtc tcgccttcgc ggattggtca ccaatgtctc caactacaac     900
gcctggaagc tatccagcaa gccagactac acggagagca cccccaacta cgacgagcag     960
aagtacatcc acgctctgtc tcctcttctt gagcaggagg gctggcccgg tgccaagttc    1020
atcgtcgatc aaggtcgatc gggaaagcag cctaccggac agaaggcttg gggagactgg    1080
tgcaatgctc ccggcaccgg atttggtctc cgcccatccg caaacactgg ggacgccttg    1140
gtcgatgctt ttgtctgggt caagccaggc ggcgagtctg acggcaccag cgacaccagt    1200
gcggctcgat acgactacca ctgtggtgct tctgccgcct tgcaaccggc gcctgaggct    1260
ggtacctggt tccaagccta ctttgagcag cttctcaaga acgcaaaccc atcgttcctg    1320
taa                                                                  1323
```

<210> SEQ ID NO 10
<211> LENGTH: 440
<212> TYPE: PRT
<213> ORGANISM: Artificial Sequence
<220> FEATURE:
<223> OTHER INFORMATION: Clone 139F12

<400> SEQUENCE: 10

Ala Pro Val Glu Glu Arg Gln Ser Cys Ser Asn Gly Val Trp Ser Gln
1               5                   10                  15

```
Cys Gly Gly Gln Asn Trp Ser Gly Thr Pro Cys Cys Thr Ser Gly Asn
                20                  25                  30

Lys Cys Val Lys Val Asn Asp Phe Tyr Ser Gln Cys Gln Pro Gly Ser
            35                  40                  45

Ala Asp Pro Ser Pro Thr Ser Thr Ile Val Ser Ala Thr Thr Thr Lys
 50                  55                  60

Ala Thr Thr Thr Gly Ser Gly Gly Ser Val Thr Ser Pro Pro Pro Val
65                  70                  75                  80

Ala Thr Asn Asn Pro Phe Ser Gly Val Asp Leu Trp Ala Asn Asn Tyr
                85                  90                  95

Tyr Arg Ser Glu Val Ser Thr Leu Ala Ile Pro Lys Leu Ser Gly Ala
            100                 105                 110

Met Ala Thr Ala Ala Ala Lys Val Ala Asp Val Pro Ser Phe Gln Trp
        115                 120                 125

Met Asp Thr Tyr Asp His Ile Ser Phe Met Glu Glu Ser Leu Ala Asp
        130                 135                 140

Ile Arg Lys Ala Asn Lys Ala Gly Gly Asn Tyr Ala Gly Gln Phe Val
145                 150                 155                 160

Val Tyr Asp Leu Pro Asp Arg Asp Cys Ala Ala Ala Ser Asn Gly
            165                 170                 175

Glu Tyr Ser Leu Asp Lys Asp Gly Lys Asn Lys Tyr Lys Ala Tyr Ile
            180                 185                 190

Ala Lys Ile Lys Gly Ile Leu Gln Asp Tyr Ser Asp Thr Arg Ile Ile
        195                 200                 205

Leu Val Ile Glu Pro Asp Ser Leu Ala Asn Met Val Thr Asn Met Asn
210                 215                 220

Val Pro Lys Cys Ala Asn Ala Ala Ser Ala Tyr Lys Glu Leu Thr Ile
225                 230                 235                 240

His Ala Leu Lys Glu Leu Asn Leu Pro Asn Val Ser Met Tyr Ile Asp
            245                 250                 255

Ala Gly His Gly Gly Trp Leu Gly Trp Pro Ala Asn Leu Pro Pro Ala
        260                 265                 270

Ala Gln Leu Tyr Gly Gln Leu Tyr Lys Asp Ala Gly Lys Pro Ser Arg
        275                 280                 285

Leu Arg Gly Leu Val Thr Asn Val Ser Asn Tyr Asn Ala Trp Lys Leu
290                 295                 300

Ser Ser Lys Pro Asp Tyr Thr Glu Ser Asn Pro Asn Tyr Asp Glu Gln
305                 310                 315                 320

Lys Tyr Ile His Ala Leu Ser Pro Leu Leu Glu Gln Glu Gly Trp Pro
            325                 330                 335

Gly Ala Lys Phe Ile Val Asp Gln Gly Arg Ser Gly Lys Gln Pro Thr
        340                 345                 350

Gly Gln Lys Ala Trp Gly Asp Trp Cys Asn Ala Pro Gly Thr Gly Phe
        355                 360                 365

Gly Leu Arg Pro Ser Ala Asn Thr Gly Asp Ala Leu Val Asp Ala Phe
        370                 375                 380

Val Trp Val Lys Pro Gly Gly Glu Ser Asp Gly Thr Ser Asp Thr Ser
385                 390                 395                 400

Ala Ala Arg Tyr Asp Tyr His Cys Gly Ala Ser Ala Ala Leu Gln Pro
            405                 410                 415

Ala Pro Glu Ala Gly Thr Trp Phe Gln Ala Tyr Phe Glu Gln Leu Leu
        420                 425                 430

Lys Asn Ala Asn Pro Ser Phe Leu
```

435                 440

<210> SEQ ID NO 11
<211> LENGTH: 1323
<212> TYPE: DNA
<213> ORGANISM: Artificial Sequence
<220> FEATURE:
<223> OTHER INFORMATION: Clone 157B11

<400> SEQUENCE: 11

| | | |
|---|---|---|
| gctcctgttg aagagcgtca gtcttgcagc aacggagtct ggtctcaatg tggtggtcag | 60 |
| aactggtccg gtactccttg ctgcaccagt ggaaacaagt gtgtcaaggt caacgacttc | 120 |
| tactcccagt gccagcctgg atctgcagac ccttctccca catccaccat tgtctccgcg | 180 |
| acgaccacca aggctactac tactggtagt ggaggctctg tcacctcgcc tcctcctgtt | 240 |
| gccaccaaca acccttttc tggggtcgat ctgtgggcca ataactatta ccgctctgaa | 300 |
| gttagcactc tcgctattcc taagttgagc ggagccatgg ccactgctgc agcaaaggtc | 360 |
| gcagatgttc cctcttttca gtggatggat acttatgacc acatctcctt catggaggag | 420 |
| tctttggccg acatccgcaa ggccaacaag gctggcggta actatgccgg acagtttgtg | 480 |
| gtgtatgact tgccggatcg cgattgcgct gccgccgcct cgaatggcga atactctctc | 540 |
| gacaatgatg cgccaacaa atataaggcc tatatcgcca agattaaggg tattctccag | 600 |
| gactattccg atacccggat cattctggtt attgagcctg actctcttgc caacatggtg | 660 |
| accaacatga cgtcccaaa gtgtgccaat gctgcttcag cctacaagga gctcaccatt | 720 |
| cacgccctca aggagctgaa ccttccaaat gtttccatgt atatcgacgc tggccatggt | 780 |
| ggatggcttg gctggccggc aaaccttcct ccggccgctc agctatacgg tcagctctac | 840 |
| aaggatgcag gcaagccgtc tcgccttcgc ggattggtca ccaatgtctc caactacaac | 900 |
| gcctggaagc tatccagcaa gccagactac acggagagca ccccaacta cgacgagcag | 960 |
| aagtacatcc acgctctgtc tcctcttctt gagcaggagg gctggcccgg tgccaagttc | 1020 |
| atcgtcgatc aaggtcgatc gggaaagcag cctaccggac agaaggcttg gggagactgg | 1080 |
| tgcaatgctc ccggcaccgg atttggtctc cgcccatccg caaacactgg ggactcgttg | 1140 |
| ctggatgctt ttgtctgggt caagccaggc ggcgagtctg acggcaccag cgacaccagt | 1200 |
| gcgacccgat acgactacca ctgtggtgct tctgccgcct tgcaaccggc gcctgaggct | 1260 |
| ggtacctggt tccaagccta cttgagcag cttctcacaa cgcaaaccc atcgttcctg | 1320 |
| taa | 1323 |

<210> SEQ ID NO 12
<211> LENGTH: 440
<212> TYPE: PRT
<213> ORGANISM: Artificial Sequence
<220> FEATURE:
<223> OTHER INFORMATION: Clone 157B11

<400> SEQUENCE: 12

Ala Pro Val Glu Glu Arg Gln Ser Cys Ser Asn Gly Val Trp Ser Gln
1               5                   10                  15

Cys Gly Gly Gln Asn Trp Ser Gly Thr Pro Cys Cys Thr Ser Gly Asn
            20                  25                  30

Lys Cys Val Lys Val Asn Asp Phe Tyr Ser Gln Cys Gln Pro Gly Ser
        35                  40                  45

Ala Asp Pro Ser Pro Thr Ser Thr Ile Val Ser Ala Thr Thr Thr Lys
    50                  55                  60

Ala Thr Thr Thr Gly Ser Gly Gly Ser Val Thr Ser Pro Pro Val
65                  70                  75                  80

Ala Thr Asn Asn Pro Phe Ser Gly Val Asp Leu Trp Ala Asn Asn Tyr
            85                  90                  95

Tyr Arg Ser Glu Val Ser Thr Leu Ala Ile Pro Lys Leu Ser Gly Ala
            100                 105                 110

Met Ala Thr Ala Ala Lys Val Ala Asp Val Pro Ser Phe Gln Trp
            115                 120                 125

Met Asp Thr Tyr Asp His Ile Ser Phe Met Glu Glu Ser Leu Ala Asp
130                 135                 140

Ile Arg Lys Ala Asn Lys Ala Gly Gly Asn Tyr Ala Gly Gln Phe Val
145                 150                 155                 160

Val Tyr Asp Leu Pro Asp Arg Asp Cys Ala Ala Ala Ser Asn Gly
            165                 170                 175

Glu Tyr Ser Leu Asp Asn Asp Gly Ala Asn Lys Tyr Lys Ala Tyr Ile
            180                 185                 190

Ala Lys Ile Lys Gly Ile Leu Gln Asp Tyr Ser Asp Thr Arg Ile Ile
            195                 200                 205

Leu Val Ile Glu Pro Asp Ser Leu Ala Asn Met Val Thr Asn Met Asn
210                 215                 220

Val Pro Lys Cys Ala Asn Ala Ala Ser Ala Tyr Lys Glu Leu Thr Ile
225                 230                 235                 240

His Ala Leu Lys Glu Leu Asn Leu Pro Asn Val Ser Met Tyr Ile Asp
            245                 250                 255

Ala Gly His Gly Gly Trp Leu Gly Trp Pro Ala Asn Leu Pro Pro Ala
            260                 265                 270

Ala Gln Leu Tyr Gly Gln Leu Tyr Lys Asp Ala Gly Lys Pro Ser Arg
            275                 280                 285

Leu Arg Gly Leu Val Thr Asn Val Ser Asn Tyr Asn Ala Trp Lys Leu
            290                 295                 300

Ser Ser Lys Pro Asp Tyr Thr Glu Ser Asn Pro Asn Tyr Asp Glu Gln
305                 310                 315                 320

Lys Tyr Ile His Ala Leu Ser Pro Leu Leu Glu Gln Glu Gly Trp Pro
            325                 330                 335

Gly Ala Lys Phe Ile Val Asp Gln Gly Arg Ser Gly Lys Gln Pro Thr
            340                 345                 350

Gly Gln Lys Ala Trp Gly Asp Trp Cys Asn Ala Pro Gly Thr Gly Phe
            355                 360                 365

Gly Leu Arg Pro Ser Ala Asn Thr Gly Asp Ser Leu Leu Asp Ala Phe
            370                 375                 380

Val Trp Val Lys Pro Gly Gly Glu Ser Asp Gly Thr Ser Asp Thr Ser
385                 390                 395                 400

Ala Thr Arg Tyr Asp Tyr His Cys Gly Ala Ser Ala Ala Leu Gln Pro
            405                 410                 415

Ala Pro Glu Ala Gly Thr Trp Phe Gln Ala Tyr Phe Glu Gln Leu Leu
            420                 425                 430

Thr Asn Ala Asn Pro Ser Phe Leu
            435                 440

<210> SEQ ID NO 13
<211> LENGTH: 1323
<212> TYPE: DNA
<213> ORGANISM: Artificial Sequence
<220> FEATURE:

<223> OTHER INFORMATION: Clone 161A1

<400> SEQUENCE: 13

```
gctcctgttg aagagcgtca gtcttgcagc aacggagtct ggtctcaatg tggtggtcag      60
aactggtccg gtactccttg ctgcaccagt ggaaacaagt gtgtcaaggt caacgacttc     120
tactcccagt gccagcctgg atctgcagac ccttctccca catccaccat tgtctccgcg     180
acgaccacca aggctactac tactggtagt ggaggctctg tcacctcgcc tcctcctgtt     240
gccaccaaca acccttttc tggggtcgat ctgtgggcca ataactatta ccgctctgaa     300
gttagcactc tcgctattcc taagttgagc ggagccatgg ccactgctgc agcaaaggtc     360
gcagatgttc cctcttttca gtggatggat acttatgacc acatctcctt catggaggag     420
tctttggccg acatccgcaa ggccaacaag gctggcggta actatgccgg acagtttgtg     480
gtgtatgact tgccggatcg cgattgcgct gccgctgcct cgaatggcga atactctctt     540
gacaaggatg caagaacaa atataaggc tatatcgcca agattaaggg tattctccag     600
gactattccg atacccggat cattctggtt attgagcctg actctcttgc caacatggtg     660
accaacatga acgtcccaaa gtgtgccaat gctgcttcag cctacaagga gctcaccatt     720
cacgccctca aggagctgaa ccttccaaat gtttccatgt atatcgacgc tggccatggt     780
ggatggcttg gctggccggc aaaccttcct ccggccgctc agctatacgg tcagctctac     840
aaggatgcag gcaagccgtc tcgccttcgc ggattggtca ccaatgtctc caactacaac     900
gcctggaagc tatccagcaa gccagactac acggagagca ccccaactca cgacgagcag     960
aagtacatcc acgctctgtc tcctcttctt gagcaggagg gctggcccgg tgccaagttc    1020
atcgtcgatc aaggtcgatc gggaaagcag cctaccggac agaaggcttg gggagactgg    1080
tgcaatgctc ccggcaccgg atttggtatc cgcccatccg caaacactgg ggacgccttg    1140
gtcgatgctt ttgtctgggt caagccaggc ggcgagtctg acggcaccag cgacaccagt    1200
gcgacccgat acgactacca ctgtggtgct tctgccgcct tgcaaccggc gcctgaggct    1260
ggtacctggt ccaagcctta ctttgagcag cttctcaaga acgcaaaccc atcgttcctg    1320
taa                                                                   1323
```

<210> SEQ ID NO 14  
<211> LENGTH: 440  
<212> TYPE: PRT  
<213> ORGANISM: Artificial Sequence  
<220> FEATURE:  
<223> OTHER INFORMATION: Clone 161A1

<400> SEQUENCE: 14

```
Ala Pro Val Glu Glu Arg Gln Ser Cys Ser Asn Gly Val Trp Ser Gln
1               5                   10                  15

Cys Gly Gly Gln Asn Trp Ser Gly Thr Pro Cys Cys Thr Ser Gly Asn
            20                  25                  30

Lys Cys Val Lys Val Asn Asp Phe Tyr Ser Gln Cys Gln Pro Gly Ser
        35                  40                  45

Ala Asp Pro Ser Pro Thr Ser Thr Ile Val Ser Ala Thr Thr Thr Lys
    50                  55                  60

Ala Thr Thr Thr Gly Ser Gly Gly Ser Val Thr Ser Pro Pro Pro Val
65                  70                  75                  80

Ala Thr Asn Asn Pro Phe Ser Gly Val Asp Leu Trp Ala Asn Asn Tyr
                85                  90                  95

Tyr Arg Ser Glu Val Ser Thr Leu Ala Ile Pro Lys Leu Ser Gly Ala
```

```
            100                 105                 110
Met Ala Thr Ala Ala Ala Lys Val Ala Asp Val Pro Ser Phe Gln Trp
                115                 120                 125
Met Asp Thr Tyr Asp His Ile Ser Phe Met Glu Glu Ser Leu Ala Asp
        130                 135                 140
Ile Arg Lys Ala Asn Lys Ala Gly Gly Asn Tyr Ala Gly Gln Phe Val
145                 150                 155                 160
Val Tyr Asp Leu Pro Asp Arg Asp Cys Ala Ala Ala Ser Asn Gly
                165                 170                 175
Glu Tyr Ser Leu Asp Lys Asp Gly Lys Asn Lys Tyr Lys Ala Tyr Ile
                180                 185                 190
Ala Lys Ile Lys Gly Ile Leu Gln Asp Tyr Ser Asp Thr Arg Ile Ile
            195                 200                 205
Leu Val Ile Glu Pro Asp Ser Leu Ala Asn Met Val Thr Asn Met Asn
            210                 215                 220
Val Pro Lys Cys Ala Asn Ala Ala Ser Ala Tyr Lys Glu Leu Thr Ile
225                 230                 235                 240
His Ala Leu Lys Glu Leu Asn Leu Pro Asn Val Ser Met Tyr Ile Asp
                245                 250                 255
Ala Gly His Gly Gly Trp Leu Gly Trp Pro Ala Asn Leu Pro Pro Ala
                260                 265                 270
Ala Gln Leu Tyr Gly Gln Leu Tyr Lys Asp Ala Gly Lys Pro Ser Arg
                275                 280                 285
Leu Arg Gly Leu Val Thr Asn Val Ser Asn Tyr Asn Ala Trp Lys Leu
            290                 295                 300
Ser Ser Lys Pro Asp Tyr Thr Glu Ser Asn Pro Asn Tyr Asp Glu Gln
305                 310                 315                 320
Lys Tyr Ile His Ala Leu Ser Pro Leu Leu Glu Gln Glu Gly Trp Pro
                325                 330                 335
Gly Ala Lys Phe Ile Val Asp Gln Gly Arg Ser Gly Lys Gln Pro Thr
                340                 345                 350
Gly Gln Lys Ala Trp Gly Asp Trp Cys Asn Ala Pro Gly Thr Gly Phe
                355                 360                 365
Gly Ile Arg Pro Ser Ala Asn Thr Gly Asp Ala Leu Val Asp Ala Phe
            370                 375                 380
Val Trp Val Lys Pro Gly Gly Glu Ser Asp Gly Thr Ser Asp Thr Ser
385                 390                 395                 400
Ala Thr Arg Tyr Asp Tyr His Cys Gly Ala Ser Ala Ala Leu Gln Pro
                405                 410                 415
Ala Pro Glu Ala Gly Thr Trp Phe Gln Ala Tyr Phe Glu Gln Leu Leu
                420                 425                 430
Lys Asn Ala Asn Pro Ser Phe Leu
                435                 440

<210> SEQ ID NO 15
<211> LENGTH: 1362
<212> TYPE: DNA
<213> ORGANISM: Artificial Sequence
<220> FEATURE:
<223> OTHER INFORMATION: Clone 161C12

<400> SEQUENCE: 15
gtgcctctag aggagcggca agcttgctca agcgtctggg gccaatgtgg tggccagaat      60
tggtcgggtc cgacttgctg tgcttccgga agcacatgcg tctactccaa cgactattac     120
```

-continued

```
tcccagtgtc ttcccggcgc tgcaagctca agctcgtcca cgcgcgccgc gtcgacgact    180
tctcgagtat cccccacaac atccggtcg agctccgcga cgcctccacc tggttctact     240
actaccagag tacctccagt cggatcggga accgctacgt attcaggcaa ccctttttgtt  300 ggggtcactc cttgggccaa tgcatattac gcctctgaag ttagcagcct cgctattcct   360
agcttgactg gagccatggc cactgctgca gcagctgtcg caaaggttcc ctcttttatg   420
tggctagata ctcttgacaa gacccctctc atggagcaaa ccttggccga catccgcacc   480
gccaacaaga atggcggtaa ctatgccgga cagtttgtgg tgtatgactt gccggatcgc   540
gattgcgctg cccttgcctc gaatggcgaa tactctctcg acaatgatgg cgccaacaaa   600
tataagaact atatccaaac cattaagaag attatccaga gctattccga tatccggata   660
ctcctggtta ttgagcctga ctctcttgcc aacctggtga ccaacatgga tgtcgccaag   720
tgtgccaagg ctcatgatgc ctacatcagc ctgacgaact acgccgtcac agaactgaac   780
cttccaaatg ttgcgatgta tttggacgct ggccatgcag gatggcttgg ctggccggca   840
aaccttcctc cggccgctca gctatacggt cagctctaca aggatgcagg caagccgtct   900
cgccttcgcg gattggtcac caatgtctcc aactacaacg cctggaagct atccagcaag   960
ccagactaca cggagagcaa ccccaactac gacgagcaga agtacatcca cgctctgtct   1020
cctcttcttg agcaggaggg ctggcccggt gccaagttca tcgtcgatca aggtcgatcg   1080
ggaaagcagc ctaccggaca gaaggcttgg ggagactggt gcaatgctcc cggcaccgga   1140
tttggtctcc gcccatccgc aaacactggg gacgccttgg tcgatgcttt tgtctgggtc   1200
aagccaggcg cgagtctga cggcaccagc gacaccagtg cggctcgata cgactaccac   1260
tgtggtattg acggcgccgt caagccggcg cctgaggctg gtacctggtt ccaagcctac   1320
tttgagcagc ttctcaagaa cgcaaaccca tcgttcctgt aa                     1362
```

<210> SEQ ID NO 16
<211> LENGTH: 453
<212> TYPE: PRT
<213> ORGANISM: Artificial Sequence
<220> FEATURE:
<223> OTHER INFORMATION: Clone 161C12

<400> SEQUENCE: 16

```
Val Pro Leu Glu Glu Arg Gln Ala Cys Ser Ser Val Trp Gly Gln Cys
1               5                   10                  15

Gly Gly Gln Asn Trp Ser Gly Pro Thr Cys Cys Ala Ser Gly Ser Thr
            20                  25                  30

Cys Val Tyr Ser Asn Asp Tyr Tyr Ser Gln Cys Leu Pro Gly Ala Ala
        35                  40                  45

Ser Ser Ser Ser Thr Arg Ala Ala Ser Thr Thr Ser Arg Val Ser
    50                  55                  60

Pro Thr Thr Ser Arg Ser Ser Ala Thr Pro Pro Gly Ser Thr
65                  70                  75                  80

Thr Thr Arg Val Pro Pro Val Gly Ser Gly Thr Ala Thr Tyr Ser Gly
                85                  90                  95

Asn Pro Phe Val Gly Val Thr Pro Trp Ala Asn Ala Tyr Tyr Ala Ser
            100                 105                 110

Glu Val Ser Ser Leu Ala Ile Pro Ser Leu Thr Gly Ala Met Ala Thr
        115                 120                 125

Ala Ala Ala Ala Val Ala Lys Val Pro Ser Phe Met Trp Leu Asp Thr
    130                 135                 140
```

```
Leu Asp Lys Thr Pro Leu Met Glu Gln Thr Leu Ala Asp Ile Arg Thr
145                 150                 155                 160

Ala Asn Lys Asn Gly Gly Asn Tyr Ala Gly Gln Phe Val Val Tyr Asp
            165                 170                 175

Leu Pro Asp Arg Asp Cys Ala Ala Leu Ala Ser Asn Gly Glu Tyr Ser
        180                 185                 190

Leu Asp Asn Asp Gly Ala Asn Lys Tyr Lys Asn Tyr Ile Gln Thr Ile
    195                 200                 205

Lys Lys Ile Ile Gln Ser Tyr Ser Asp Ile Arg Ile Leu Leu Val Ile
210                 215                 220

Glu Pro Asp Ser Leu Ala Asn Leu Val Thr Asn Met Asp Val Ala Lys
225                 230                 235                 240

Cys Ala Lys Ala His Asp Ala Tyr Ile Ser Leu Thr Asn Tyr Ala Val
            245                 250                 255

Thr Glu Leu Asn Leu Pro Asn Val Ala Met Tyr Leu Asp Ala Gly His
        260                 265                 270

Ala Gly Trp Leu Gly Trp Pro Ala Asn Leu Pro Pro Ala Ala Gln Leu
    275                 280                 285

Tyr Gly Gln Leu Tyr Lys Asp Ala Gly Lys Pro Ser Arg Leu Arg Gly
290                 295                 300

Leu Val Thr Asn Val Ser Asn Tyr Asn Ala Trp Lys Leu Ser Ser Lys
305                 310                 315                 320

Pro Asp Tyr Thr Glu Ser Asn Pro Asn Tyr Asp Glu Gln Lys Tyr Ile
            325                 330                 335

His Ala Leu Ser Pro Leu Leu Glu Gln Glu Gly Trp Pro Gly Ala Lys
        340                 345                 350

Phe Ile Val Asp Gln Gly Arg Ser Gly Lys Gln Pro Thr Gly Gln Lys
    355                 360                 365

Ala Trp Gly Asp Trp Cys Asn Ala Pro Gly Thr Gly Phe Gly Leu Arg
370                 375                 380

Pro Ser Ala Asn Thr Gly Asp Ala Leu Val Asp Ala Phe Val Trp Val
385                 390                 395                 400

Lys Pro Gly Gly Glu Ser Asp Gly Thr Ser Asp Thr Ser Ala Ala Arg
            405                 410                 415

Tyr Asp Tyr His Cys Gly Ile Asp Gly Ala Val Lys Pro Ala Pro Glu
        420                 425                 430

Ala Gly Thr Trp Phe Gln Ala Tyr Phe Glu Gln Leu Leu Lys Asn Ala
    435                 440                 445

Asn Pro Ser Phe Leu
    450

<210> SEQ ID NO 17
<211> LENGTH: 1323
<212> TYPE: DNA
<213> ORGANISM: Artificial Sequence
<220> FEATURE:
<223> OTHER INFORMATION: Clone 189H8

<400> SEQUENCE: 17
gctcctgttg aagagcgtca gtcttgcagc aacggagtct ggtctcaatg tggtggtcag    60
aactggtccg gtactccttg ctgcaccagt ggaaacaagt gtgtcaaggt caacgacttc   120
tactcccagt gccagcctgg atctgcagac ccttctccca catccaccat tgtctccgcg   180
acgaccacca aggctactac tactggtagt ggaggctctg tcacctcgcc tcctcctgtt   240
gccaccaaca cccttttttc tggggtcgat ctgtgggcca ataactatta ccgctctgaa   300
```

```
gttagcactc tcgctattcc taagttgagc ggagccatgg ccactgctgc agcaaaggtc    360
gcagatgttc cctcttttca gtggatggat acttatgacc acatctccct catggaggac    420
accttggtcg acatccgcaa ggccaacctg gctggcggta actatgccgg acagtttgtg    480
gtgtatgact tgccggatcg cgattgcgct gccgctgcct cgaatggcga atactctctt    540
gacaaggatg gcaagaacaa atataaggcc tatatcgcca agattaaggg tattctccag    600
gactattccg ataccggat cattctggtt attgagcctg actctcttgc caacatggtg    660
accaacatga acgtcccaaa gtgtgccaat gctgcttcag cctacaagga gctcaccatt    720
cacgccctca aggagctgaa ccttccaaat gtttccatgt atatcgacgc tggccatggt    780
ggatggcttg gctggccggc aaaccaaggc ccggccgcta aactatttgc aagcatctac    840
aaggatgcag gcaagccggc cgctcttcgc ggattggcaa ccaatgtcgc caactacaac    900
gcctggagcc tcagcagcgc tccaccttac acgcaaggcg cctctatcta cgacgagaag    960
agcttcatcc acgctatggg acctcttctt gagcagaatg gctggcctgg tgccaagttc    1020
atcgtcgatc aaggtcgatc gggaaagcag cctaccggac agaaggcttg gggagactgg    1080
tgcaatgctc ccggcaccgg atttggtctc cgcccatccg caaacactgg ggactcgttg    1140
ctggatgctt ttgtctgggt caagccaggc ggcgagtctg acggaccag cgacaccagt    1200
gcgacccgat acgactacca ctgtggtgct tctgccgcct tgcaaccggc gcctgaggct    1260
ggtacctggt tccaagccta ctttgagcag cttctcacaa acgcaaaccc atcgttcctg    1320
taa                                                                   1323
```

<210> SEQ ID NO 18
<211> LENGTH: 440
<212> TYPE: PRT
<213> ORGANISM: Artificial Sequence
<220> FEATURE:
<223> OTHER INFORMATION: Clone 189H8

<400> SEQUENCE: 18

```
Ala Pro Val Glu Glu Arg Gln Ser Cys Ser Asn Gly Val Trp Ser Gln
1               5                   10                  15

Cys Gly Gly Gln Asn Trp Ser Gly Thr Pro Cys Cys Thr Ser Gly Asn
            20                  25                  30

Lys Cys Val Lys Val Asn Asp Phe Tyr Ser Gln Cys Gln Pro Gly Ser
        35                  40                  45

Ala Asp Pro Ser Pro Thr Ser Thr Ile Val Ser Ala Thr Thr Thr Lys
    50                  55                  60

Ala Thr Thr Thr Gly Ser Gly Gly Ser Val Thr Ser Pro Pro Pro Val
65                  70                  75                  80

Ala Thr Asn Asn Pro Phe Ser Gly Val Asp Leu Trp Ala Asn Asn Tyr
                85                  90                  95

Tyr Arg Ser Glu Val Ser Thr Leu Ala Ile Pro Lys Leu Ser Gly Ala
            100                 105                 110

Met Ala Thr Ala Ala Lys Val Ala Asp Val Pro Ser Phe Gln Trp
        115                 120                 125

Met Asp Thr Tyr Asp His Ile Ser Leu Met Glu Asp Thr Leu Val Asp
    130                 135                 140

Ile Arg Lys Ala Asn Leu Ala Gly Gly Asn Tyr Ala Gly Gln Phe Val
145                 150                 155                 160

Val Tyr Asp Leu Pro Asp Arg Asp Cys Ala Ala Ala Ser Asn Gly
                165                 170                 175
```

Glu Tyr Ser Leu Asp Lys Asp Gly Lys Asn Lys Tyr Lys Ala Tyr Ile
            180                 185                 190

Ala Lys Ile Lys Gly Ile Leu Gln Asp Tyr Ser Asp Thr Arg Ile Ile
        195                 200                 205

Leu Val Ile Glu Pro Asp Ser Leu Ala Asn Met Val Thr Asn Met Asn
210                 215                 220

Val Pro Lys Cys Ala Asn Ala Ala Ser Ala Tyr Lys Glu Leu Thr Ile
225                 230                 235                 240

His Ala Leu Lys Glu Leu Asn Leu Pro Asn Val Ser Met Tyr Ile Asp
                245                 250                 255

Ala Gly His Gly Gly Trp Leu Gly Trp Pro Ala Asn Gln Gly Pro Ala
            260                 265                 270

Ala Lys Leu Phe Ala Ser Ile Tyr Lys Asp Ala Gly Lys Pro Ala Ala
        275                 280                 285

Leu Arg Gly Leu Ala Thr Asn Val Ala Asn Tyr Asn Ala Trp Ser Leu
    290                 295                 300

Ser Ser Ala Pro Pro Tyr Thr Gln Gly Ala Ser Ile Tyr Asp Glu Lys
305                 310                 315                 320

Ser Phe Ile His Ala Met Gly Pro Leu Leu Glu Gln Asn Gly Trp Pro
                325                 330                 335

Gly Ala Lys Phe Ile Val Asp Gln Gly Arg Ser Gly Lys Gln Pro Thr
            340                 345                 350

Gly Gln Lys Ala Trp Gly Asp Trp Cys Asn Ala Pro Gly Thr Gly Phe
        355                 360                 365

Gly Leu Arg Pro Ser Ala Asn Thr Gly Asp Ser Leu Leu Asp Ala Phe
    370                 375                 380

Val Trp Val Lys Pro Gly Gly Glu Ser Asp Gly Thr Ser Asp Thr Ser
385                 390                 395                 400

Ala Thr Arg Tyr Asp Tyr His Cys Gly Ala Ser Ala Ala Leu Gln Pro
                405                 410                 415

Ala Pro Glu Ala Gly Thr Trp Phe Gln Ala Tyr Phe Glu Gln Leu Leu
            420                 425                 430

Thr Asn Ala Asn Pro Ser Phe Leu
        435                 440

<210> SEQ ID NO 19
<211> LENGTH: 1362
<212> TYPE: DNA
<213> ORGANISM: Artificial Sequence
<220> FEATURE:
<223> OTHER INFORMATION: Clone 196D9

<400> SEQUENCE: 19
gtgcctctag aggagcggca agcttgctca agcgtctggg gccaatgtgg tggccagaat      60
tggtcgggtc cgacttgctg tgcttccgga agcacatgcg tctactccaa cgactattac     120
tcccagtgtc ttcccggcgc tgcaagctca agctcgtcca cgcgcgccgc gtcgacgact     180
tctcgagtat ccccacaac atccggtcg agctccgcga cgcctccacc tggttctact       240
actaccagag tacctccagt cggatcggga accgctacgt attcaggcaa ccctttgtt     300 ggggtcactc cttgggccaa tgcatattac gcctctgaag ttagcagcct cgctattcct    360
agcttgactg gagccatggc cactgctgca gcagctgtcg caaaggttcc ctctttatg     420 tggctagata tcttgacaa gacccctctc atggagcaaa ccttggccga catccgcacc     480
gccaacaaga atggcggtaa ctatgccgga cagtttgtgg tgtatgactt gccggatcgc    540

```
gattgcgctg cccttgcctc gaatggcgaa tactctattg ccgatggtgg cgtcgccaaa      600
tataagaact atatcgacac cattcgtcaa attgtcgtgg aatattccga tatccggacc      660
ctcctggtta ttgagcctga ctctcttacc aacctggtga ccaacatgaa cgtcccaaag      720
tgtgccaatg ctcagtcagc ctaccttgag tgcatcaact acgccgtcac acagctgaac      780
cttccaaatg ttgcgatgta tttggacgct ggccatgcag gatggcttgg ctggccggca      840
aaccaagacc cggccgctca gctatttgca aatgtttaca agaatgcatc gtctccgaga      900
gctcttcgcg gattggcaac caatgtcgcc aactacaacg ggtggaacat taccagcccc      960
ccatcgtaca cgcaaggcaa cgctgtctac aacgagaagc tgtacatcca cgctattgga     1020
cctcttcttg ccaatcacgg ctggtccaac gccttcttca tcactgatca aggtcgatcg     1080
ggaaagcagc ctaccggaca gcaacagtgg ggagactggt gcaatgctcc cggcaccgga     1140
tttggtctcc gcccatccgc aaacactggg gacgccttgg tcgatgcttt tgtctgggtc     1200
aagccaggcg gcgagtctga cggcaccagc gacaccagtg cggctcgata cgactaccac     1260
tgtggtattg acggcgccgt caagccggcg cctgaggctg gtacctggtt ccaagcctac     1320
tttgagcagc ttctcaagaa cgcaaaccca tcgttcctgt aa                        1362
```

<210> SEQ ID NO 20
<211> LENGTH: 453
<212> TYPE: PRT
<213> ORGANISM: Artificial Sequence
<220> FEATURE:
<223> OTHER INFORMATION: Clone 196D9

<400> SEQUENCE: 20

```
Val Pro Leu Glu Glu Arg Gln Ala Cys Ser Ser Val Trp Gly Gln Cys
1               5                   10                  15

Gly Gly Gln Asn Trp Ser Gly Pro Thr Cys Cys Ala Ser Gly Ser Thr
            20                  25                  30

Cys Val Tyr Ser Asn Asp Tyr Tyr Ser Gln Cys Leu Pro Gly Ala Ala
        35                  40                  45

Ser Ser Ser Ser Thr Arg Ala Ala Ser Thr Thr Ser Arg Val Ser
    50                  55                  60

Pro Thr Thr Ser Arg Ser Ser Ala Thr Pro Pro Gly Ser Thr
65                  70                  75                  80

Thr Thr Arg Val Pro Pro Val Gly Ser Gly Thr Ala Thr Tyr Ser Gly
                85                  90                  95

Asn Pro Phe Val Gly Val Thr Pro Trp Ala Asn Ala Tyr Tyr Ala Ser
            100                 105                 110

Glu Val Ser Ser Leu Ala Ile Pro Ser Leu Thr Gly Ala Met Ala Thr
        115                 120                 125

Ala Ala Ala Ala Val Ala Lys Val Pro Ser Phe Met Trp Leu Asp Thr
    130                 135                 140

Leu Asp Lys Thr Pro Leu Met Glu Gln Thr Leu Ala Asp Ile Arg Thr
145                 150                 155                 160

Ala Asn Lys Asn Gly Gly Asn Tyr Ala Gly Gln Phe Val Val Tyr Asp
                165                 170                 175

Leu Pro Asp Arg Asp Cys Ala Ala Leu Ala Ser Asn Gly Glu Tyr Ser
            180                 185                 190

Ile Ala Asp Gly Gly Val Ala Lys Tyr Lys Asn Tyr Ile Asp Thr Ile
        195                 200                 205

Arg Gln Ile Val Val Glu Tyr Ser Asp Ile Arg Thr Leu Leu Val Ile
```

```
                210                 215                 220
Glu Pro Asp Ser Leu Thr Asn Leu Val Thr Asn Met Asn Val Pro Lys
225                 230                 235                 240

Cys Ala Asn Ala Gln Ser Ala Tyr Leu Glu Cys Ile Asn Tyr Ala Val
                245                 250                 255

Thr Gln Leu Asn Leu Pro Asn Val Ala Met Tyr Leu Asp Ala Gly His
                260                 265                 270

Ala Gly Trp Leu Gly Trp Pro Ala Asn Gln Asp Pro Ala Ala Gln Leu
            275                 280                 285

Phe Ala Asn Val Tyr Lys Asn Ala Ser Ser Pro Arg Ala Leu Arg Gly
        290                 295                 300

Leu Ala Thr Asn Val Ala Asn Tyr Asn Gly Trp Asn Ile Thr Ser Pro
305                 310                 315                 320

Pro Ser Tyr Thr Gln Gly Asn Ala Val Tyr Asn Glu Lys Leu Tyr Ile
                325                 330                 335

His Ala Ile Gly Pro Leu Leu Ala Asn His Gly Trp Ser Asn Ala Phe
                340                 345                 350

Phe Ile Thr Asp Gln Gly Arg Ser Gly Lys Gln Pro Thr Gly Gln Gln
            355                 360                 365

Gln Trp Gly Asp Trp Cys Asn Ala Pro Gly Thr Gly Phe Gly Leu Arg
        370                 375                 380

Pro Ser Ala Asn Thr Gly Asp Ala Leu Val Asp Ala Phe Val Trp Val
385                 390                 395                 400

Lys Pro Gly Gly Glu Ser Asp Gly Thr Ser Asp Thr Ser Ala Ala Arg
                405                 410                 415

Tyr Asp Tyr His Cys Gly Ile Asp Gly Ala Val Lys Pro Ala Pro Glu
                420                 425                 430

Ala Gly Thr Trp Phe Gln Ala Tyr Phe Glu Gln Leu Leu Lys Asn Ala
            435                 440                 445

Asn Pro Ser Phe Leu
    450

<210> SEQ ID NO 21
<211> LENGTH: 1362
<212> TYPE: DNA
<213> ORGANISM: Artificial Sequence
<220> FEATURE:
<223> OTHER INFORMATION: Clone 198E11

<400> SEQUENCE: 21
gtgcctctag aggagcggca agcttgctca agcgtctggg gccaatgtgg tggccagaat    60
tggtcgggtc cgacttgctg tgcttccgga agcacatgcg tctactccaa cgactattac   120
tcccagtgtc ttcccggcgc tgcaagctca agctcgtcca cgcgcgccgc gtcgacgact   180
tctcgagtat cccccacaac atcccggtcg agctccgcga cgcctccacc tggttctact   240
actaccagag tacctccagt cggatcggga accgctacgt attcaggcaa ccctttttgtt   300 ggggtcactc cttgggccaa tgcatattac gcctctgaag ttagcagcct cgctattcct   360
agcttgactg gagccatggc cactgctgca gcagctgtcg caaaggttcc ctcttttatg   420
tggctagata ctcttgacaa gacccctctc atggagcaaa ccttggccga catccgcacc   480
gccaacaaga tggcggtaa ctatgccgga cagtttgtgg tgtatgactt gccggatcgc   540
gattgcgctg ccgctgcctc gaatggcgaa tactctcttg acaaggatgg caagaacaaa   600
tataaggcct atatcgccaa gattaagggt attctccagg actattccga tacccggatc   660
```

```
attctggtta ttgagcctga ctctcttgcc aacatggtga ccaacatgaa cgtcccaaag      720
tgtgccaatg ctgcttcagc ctacaaggag ctcaccattc acgccctcaa ggagctgaac      780
cttccaaatg tttccatgta tatcgacgct ggccatggtg gatggcttgg ctggccggca      840
aaccttcctc cggccgctca gctatacggt cagctctaca aggatgcagg caagccgtct      900
cgccttcgcg gattggtcac caatgtctcc aactacaacg cctggaagct atccagcaag      960
ccagactaca cggagagcaa ccccaactac gacgagcaga agtacatcca cgctctgtct     1020
cctcttcttg agcaggaggg ctggcccggt gccaagttca tcgtcgatca aggtcgatcg     1080
ggaaagcagc ctaccggaca gaaggcttgg ggagactggt gcaatgtgat cggcaccgga     1140
tttggtattc gcccatccgc aaacactggg gactcgttgc tggattcgtt tgtctgggtc     1200
aagccaggcg gcgagtctga cggcaccagc gacaccagtg cgacccgata cgactaccac     1260
tgtggtgctt ctgccgcctt gcaaccggcg cctgaggctg gtacctggtt ccaagcctac     1320
tttgagcagc ttctcacaaa cgcaaaccca tcgttcctgt aa                        1362
```

<210> SEQ ID NO 22
<211> LENGTH: 453
<212> TYPE: PRT
<213> ORGANISM: Artificial Sequence
<220> FEATURE:
<223> OTHER INFORMATION: Clone 198E11

<400> SEQUENCE: 22

```
Val Pro Leu Glu Glu Arg Gln Ala Cys Ser Ser Val Trp Gly Gln Cys
1               5                   10                  15

Gly Gly Gln Asn Trp Ser Gly Pro Thr Cys Cys Ala Ser Gly Ser Thr
            20                  25                  30

Cys Val Tyr Ser Asn Asp Tyr Tyr Ser Gln Cys Leu Pro Gly Ala Ala
        35                  40                  45

Ser Ser Ser Ser Thr Arg Ala Ala Ser Thr Thr Ser Arg Val Ser
    50                  55                  60

Pro Thr Thr Ser Arg Ser Ser Ala Thr Pro Pro Gly Ser Thr
65                  70                  75                  80

Thr Thr Arg Val Pro Pro Val Gly Ser Gly Thr Ala Tyr Ser Gly
                85                  90                  95

Asn Pro Phe Val Gly Val Thr Pro Trp Ala Asn Ala Tyr Tyr Ala Ser
            100                 105                 110

Glu Val Ser Ser Leu Ala Ile Pro Ser Leu Thr Gly Ala Met Ala Thr
        115                 120                 125

Ala Ala Ala Val Ala Lys Val Pro Ser Phe Met Trp Leu Asp Thr
    130                 135                 140

Leu Asp Lys Thr Pro Leu Met Glu Gln Thr Leu Ala Asp Ile Arg Thr
145                 150                 155                 160

Ala Asn Lys Asn Gly Gly Asn Tyr Ala Gly Gln Phe Val Val Tyr Asp
                165                 170                 175

Leu Pro Asp Arg Asp Cys Ala Ala Ala Ser Asn Gly Glu Tyr Ser
            180                 185                 190

Leu Asp Lys Asp Gly Lys Asn Lys Tyr Lys Ala Tyr Ile Ala Lys Ile
        195                 200                 205

Lys Gly Ile Leu Gln Asp Tyr Ser Asp Thr Arg Ile Ile Leu Val Ile
    210                 215                 220

Glu Pro Asp Ser Leu Ala Asn Met Val Thr Asn Met Asn Val Pro Lys
225                 230                 235                 240
```

```
        Cys Ala Asn Ala Ala Ser Ala Tyr Lys Glu Leu Thr Ile His Ala Leu
                        245                 250                 255

Lys Glu Leu Asn Leu Pro Asn Val Ser Met Tyr Ile Asp Ala Gly His
                    260                 265                 270

Gly Gly Trp Leu Gly Trp Pro Ala Asn Leu Pro Pro Ala Ala Gln Leu
                275                 280                 285

Tyr Gly Gln Leu Tyr Lys Asp Ala Gly Lys Pro Ser Arg Leu Arg Gly
            290                 295                 300

Leu Val Thr Asn Val Ser Asn Tyr Asn Ala Trp Lys Leu Ser Ser Lys
        305                 310                 315                 320

Pro Asp Tyr Thr Glu Ser Asn Pro Asn Tyr Asp Glu Gln Lys Tyr Ile
                        325                 330                 335

His Ala Leu Ser Pro Leu Leu Glu Gln Glu Gly Trp Pro Gly Ala Lys
                    340                 345                 350

Phe Ile Val Asp Gln Gly Arg Ser Gly Lys Gln Pro Thr Gly Gln Lys
                355                 360                 365

Ala Trp Gly Asp Trp Cys Asn Val Ile Gly Thr Gly Phe Gly Ile Arg
            370                 375                 380

Pro Ser Ala Asn Thr Gly Asp Ser Leu Leu Asp Ser Phe Val Trp Val
        385                 390                 395                 400

Lys Pro Gly Gly Glu Ser Asp Gly Thr Ser Asp Thr Ser Ala Thr Arg
                        405                 410                 415

Tyr Asp Tyr His Cys Gly Ala Ser Ala Ala Leu Gln Pro Ala Pro Glu
                    420                 425                 430

Ala Gly Thr Trp Phe Gln Ala Tyr Phe Glu Gln Leu Leu Thr Asn Ala
                435                 440                 445

Asn Pro Ser Phe Leu
            450

<210> SEQ ID NO 23
<211> LENGTH: 1323
<212> TYPE: DNA
<213> ORGANISM: Artificial Sequence
<220> FEATURE:
<223> OTHER INFORMATION: Clone 251B4

<400> SEQUENCE: 23
gctcctgttg aagagcgtca gtcttgcagc aacggagtct ggtctcaatg tggtggtcag    60
aactggtccg gtactccttg ctgcaccagt ggaaacaagt gtgtcaaggt caacgacttc   120
tactcccagt gccagcctgg atctgcagac ccttctccca catccaccat tgtctccgcg   180
acgaccacca aggctactac tactggtagt ggaggctctg tcacctcgcc tcctcctgtt   240
gccaccaaca ccccttttc tggggtcgat ctgtgggcca ataactatta ccgctctgaa   300
gttagcactc tcgctattcc taagttgagc ggagccatgg ccactgctgc agcaaaggtc   360
gcagatgttc cctcttttca gtggatggat acttatgacc acatctcctt catggaggag   420
tctttggccg acatccgcac cgccaacaag aatggcggta actatgccgg acagtttgtg   480
gtgtatgact tgccggatcg cgattgcgct gccgccgcct cgaatggcga atactctctc   540
gacaatgatg cgccaacaa atataagaac tatatccaaa ccattaagaa gattatccag   600
agctattccg atatccggat actcctggtt attgagcctg actctcttgc caacctggtg   660
accaacatgg atgtcgccaa gtgtgccaag gctcatgatg cctacatcag cctgacgaac   720
tacgccgtca cagaactgaa ccttccaaat gttgcgatgt atttggacgc tggccatgca   780
ggatggcttg gctggccggc aaaccaaggc ccggccgcta actatttgc aagcatctac   840
```

```
aaggatgcag gcaagccggc cgctcttcgc ggattggcaa ccaatgtcgc caactacaac      900
gcctggaagc tatccagcaa gccagactac acggagagca accccaacta cgacgagcag      960
aagtacatcc acgctctgtc tcctcttctt gagcaggagg gctggcccgg tgccaagttc     1020
atcgtcgatc aaggtcgatc gggaaagcag cctaccggac agaaggcttg gggagactgg     1080
tgcaatgctc ccggcaccgg atttggtctc cgcccatccg caaacactgg ggacgccttg     1140
gtcgatgctt ttgtctgggt caagccaggc ggcgagtgtg acggcaccag cgacaccagt     1200
gcggctcgat acgactacca ctgtggtatt gacggcgccg tcaagccggc gcctgaggct     1260
ggtacctggt tccaagccta ctttgagcag cttctcacaa acgcaaaccc atcgttcctg     1320
taa                                                                   1323
```

<210> SEQ ID NO 24
<211> LENGTH: 440
<212> TYPE: PRT
<213> ORGANISM: Artificial Sequence
<220> FEATURE:
<223> OTHER INFORMATION: Clone 251B4

<400> SEQUENCE: 24

```
Ala Pro Val Glu Glu Arg Gln Ser Cys Ser Asn Gly Val Trp Ser Gln
1               5                   10                  15
Cys Gly Gly Gln Asn Trp Ser Gly Thr Pro Cys Cys Thr Ser Gly Asn
            20                  25                  30
Lys Cys Val Lys Val Asn Asp Phe Tyr Ser Gln Cys Gln Pro Gly Ser
        35                  40                  45
Ala Asp Pro Ser Pro Thr Ser Thr Ile Val Ser Ala Thr Thr Thr Lys
    50                  55                  60
Ala Thr Thr Thr Gly Ser Gly Gly Ser Val Thr Ser Pro Pro Pro Val
65                  70                  75                  80
Ala Thr Asn Asn Pro Phe Ser Gly Val Asp Leu Trp Ala Asn Asn Tyr
                85                  90                  95
Tyr Arg Ser Glu Val Ser Thr Leu Ala Ile Pro Lys Leu Ser Gly Ala
            100                 105                 110
Met Ala Thr Ala Ala Ala Lys Val Ala Asp Val Pro Ser Phe Gln Trp
        115                 120                 125
Met Asp Thr Tyr Asp His Ile Ser Phe Met Glu Glu Ser Leu Ala Asp
    130                 135                 140
Ile Arg Thr Ala Asn Lys Asn Gly Gly Asn Tyr Ala Gly Gln Phe Val
145                 150                 155                 160
Val Tyr Asp Leu Pro Asp Arg Asp Cys Ala Ala Ala Ser Asn Gly
                165                 170                 175
Glu Tyr Ser Leu Asp Asn Asp Gly Ala Asn Lys Tyr Lys Asn Tyr Ile
            180                 185                 190
Gln Thr Ile Lys Lys Ile Ile Gln Ser Tyr Ser Asp Ile Arg Ile Leu
        195                 200                 205
Leu Val Ile Glu Pro Asp Ser Leu Ala Asn Leu Val Thr Asn Met Asp
    210                 215                 220
Val Ala Lys Cys Ala Lys Ala His Asp Ala Tyr Ile Ser Leu Thr Asn
225                 230                 235                 240
Tyr Ala Val Thr Glu Leu Asn Leu Pro Asn Val Ala Met Tyr Leu Asp
                245                 250                 255
Ala Gly His Ala Gly Trp Leu Gly Trp Pro Ala Asn Gln Gly Pro Ala
            260                 265                 270
```

```
Ala Lys Leu Phe Ala Ser Ile Tyr Lys Asp Ala Gly Lys Pro Ala Ala
        275                 280                 285

Leu Arg Gly Leu Ala Thr Asn Val Ala Asn Tyr Asn Ala Trp Lys Leu
    290                 295                 300

Ser Ser Lys Pro Asp Tyr Thr Glu Ser Asn Pro Asn Tyr Asp Glu Gln
305                 310                 315                 320

Lys Tyr Ile His Ala Leu Ser Pro Leu Leu Glu Gln Glu Gly Trp Pro
                325                 330                 335

Gly Ala Lys Phe Ile Val Asp Gln Gly Arg Ser Gly Lys Gln Pro Thr
            340                 345                 350

Gly Gln Lys Ala Trp Gly Asp Trp Cys Asn Ala Pro Gly Thr Gly Phe
        355                 360                 365

Gly Leu Arg Pro Ser Ala Asn Thr Gly Asp Ala Leu Val Asp Ala Phe
    370                 375                 380

Val Trp Val Lys Pro Gly Gly Glu Cys Asp Gly Thr Ser Asp Thr Ser
385                 390                 395                 400

Ala Ala Arg Tyr Asp Tyr His Cys Gly Ile Asp Gly Ala Val Lys Pro
                405                 410                 415

Ala Pro Glu Ala Gly Thr Trp Phe Gln Ala Tyr Phe Glu Gln Leu Leu
            420                 425                 430

Thr Asn Ala Asn Pro Ser Phe Leu
        435                 440

<210> SEQ ID NO 25
<211> LENGTH: 1362
<212> TYPE: DNA
<213> ORGANISM: Artificial Sequence
<220> FEATURE:
<223> OTHER INFORMATION: Clone 251C4

<400> SEQUENCE: 25
gtgcctctag aggagcggca agcttgctca agcgtctggg gccaatgtgg tggccagaat       60
tggtcgggtc cgacttgctg tgcttccgga agcacatgcg tctactccaa cgactattac      120
tcccagtgtc ttcccggcgc tgcaagctca agctcgtcca cgcgcgccgc gtcgacgact      180
tctcgagtat cccccacaac atcccggtcg agctccgcga cgcctccacc tggttctact      240
actaccagag tacctccagt cggatcggga accgctacgt attcaggcaa cccttttgtt      300
ggggtcactc cttgggccaa tgcatattac gcctctgaag ttagcagcct cgctattcct      360
agcttgactg gagccatggc cactgctgca gcagctgtcg caaaggttcc ctcttttatg      420
tggctagata ctcttgacaa gacccctctc atggagcaaa ccttggccga catccgcacc      480
gccaacaaga atggcggtaa ctatgccgga cagtttgtgg tgtatgactt gccggatcgc      540
gattgcgctg ccgctgcctc gaatggcgaa tactctattg ccgatggtgg cgtcgccaaa      600
tataagaact atatcgacac cattcgtcaa attgtcgtgg aatattccga tatccggacc      660
ctcctggtta ttgagcctga ctctcttgcc aacctggtga ccaacctcgg tactccaaag      720
tgtgccaatg ctcagtcagc ctaccttgag tgcatcaact acgccgtcac acagctgaac      780
cttccaaatg ttgcgatgta tttggacgct ggccatgcag atggcttggg ctggccggca      840
aaccaagacc cggccgctca gctatttgca aatgtttaca gaatgcatc gtctccgaga      900 gctcttcgcg gattggcaac caatgtcgcc aactacaacg ggtggaacat taccagcccc      960
ccatcgtaca cgcaaggcaa cgctgtctac aacgagaagc tgtacatcca cgctattgga     1020
cctcttcttg ccaatcacgg ctggtccaac gccttcttca tcactgatca aggtcgatcg     1080
```

```
ggaaagcagc ctaccggaca gcaacagtgg ggagactggt gcaatgtgat cggcaccgga    1140
tttggtattc gcccatccgc aaacactggg gactcgttgc tggattcgtt tgtctgggtc    1200
aagccaggcg gcgagtgtga cggcaccagc gacaccagtg cgccacgatt tgactcccac    1260
tgtgcgctcc cagatgcctt gcaaccggcg cctgaggctg gtacctggtt ccaagcctac    1320
tttgagcagc ttctcacaaa cgcaaaccca tcgttcctgt aa                       1362
```

<210> SEQ ID NO 26
<211> LENGTH: 453
<212> TYPE: PRT
<213> ORGANISM: Artificial Sequence
<220> FEATURE:
<223> OTHER INFORMATION: Clone 251C4

<400> SEQUENCE: 26

```
Val Pro Leu Glu Glu Arg Gln Ala Cys Ser Ser Val Trp Gly Gln Cys
1               5                  10                  15

Gly Gly Gln Asn Trp Ser Gly Pro Thr Cys Cys Ala Ser Gly Ser Thr
            20                  25                  30

Cys Val Tyr Ser Asn Asp Tyr Tyr Ser Gln Cys Leu Pro Gly Ala Ala
        35                  40                  45

Ser Ser Ser Ser Thr Arg Ala Ala Ser Thr Thr Ser Arg Val Ser
    50                  55                  60

Pro Thr Thr Ser Arg Ser Ser Ala Thr Pro Pro Gly Ser Thr
65                  70                  75                  80

Thr Thr Arg Val Pro Pro Val Gly Ser Gly Thr Ala Thr Tyr Ser Gly
                85                  90                  95

Asn Pro Phe Val Gly Val Thr Pro Trp Ala Asn Ala Tyr Tyr Ala Ser
            100                 105                 110

Glu Val Ser Ser Leu Ala Ile Pro Ser Leu Thr Gly Ala Met Ala Thr
        115                 120                 125

Ala Ala Ala Ala Val Ala Lys Val Pro Ser Phe Met Trp Leu Asp Thr
    130                 135                 140

Leu Asp Lys Thr Pro Leu Met Glu Gln Thr Leu Ala Asp Ile Arg Thr
145                 150                 155                 160

Ala Asn Lys Asn Gly Gly Asn Tyr Ala Gly Gln Phe Val Val Tyr Asp
                165                 170                 175

Leu Pro Asp Arg Asp Cys Ala Ala Ala Ser Asn Gly Glu Tyr Ser
            180                 185                 190

Ile Ala Asp Gly Gly Val Ala Lys Tyr Lys Asn Tyr Ile Asp Thr Ile
        195                 200                 205

Arg Gln Ile Val Val Glu Tyr Ser Asp Ile Arg Thr Leu Leu Val Ile
    210                 215                 220

Glu Pro Asp Ser Leu Ala Asn Leu Val Thr Asn Leu Gly Thr Pro Lys
225                 230                 235                 240

Cys Ala Asn Ala Gln Ser Ala Tyr Leu Glu Cys Ile Asn Tyr Ala Val
                245                 250                 255

Thr Gln Leu Asn Leu Pro Asn Val Ala Met Tyr Leu Asp Ala Gly His
            260                 265                 270

Ala Gly Trp Leu Gly Trp Pro Ala Asn Gln Asp Pro Ala Ala Gln Leu
        275                 280                 285

Phe Ala Asn Val Tyr Lys Asn Ala Ser Ser Pro Arg Ala Leu Arg Gly
    290                 295                 300

Leu Ala Thr Asn Val Ala Asn Tyr Asn Gly Trp Asn Ile Thr Ser Pro
```

```
            305                 310                 315                 320
Pro Ser Tyr Thr Gln Gly Asn Ala Val Tyr Asn Glu Lys Leu Tyr Ile
                325                 330                 335

His Ala Ile Gly Pro Leu Leu Ala Asn His Gly Trp Ser Asn Ala Phe
                340                 345                 350

Phe Ile Thr Asp Gln Gly Arg Ser Gly Lys Gln Pro Thr Gly Gln Gln
                355                 360                 365

Gln Trp Gly Asp Trp Cys Asn Val Ile Gly Thr Gly Phe Gly Ile Arg
                370                 375                 380

Pro Ser Ala Asn Thr Gly Asp Ser Leu Leu Asp Ser Phe Val Trp Val
385                 390                 395                 400

Lys Pro Gly Gly Glu Cys Asp Gly Thr Ser Asp Thr Ser Ala Pro Arg
                405                 410                 415

Phe Asp Ser His Cys Ala Leu Pro Asp Ala Leu Gln Pro Ala Pro Glu
                420                 425                 430

Ala Gly Thr Trp Phe Gln Ala Tyr Phe Glu Gln Leu Leu Thr Asn Ala
                435                 440                 445

Asn Pro Ser Phe Leu
            450

<210> SEQ ID NO 27
<211> LENGTH: 1353
<212> TYPE: DNA
<213> ORGANISM: Artificial Sequence
<220> FEATURE:
<223> OTHER INFORMATION: Clone 382A2

<400> SEQUENCE: 27
gcccctcttg ttgaggagcg ccaggcttgc gctgcccaat gggcccagtg tggtggcttc     60
agctggaatg gtgctacctg ctgccagtct ggtagctact gcagcaagat caacgactat    120
tactctcagt gcattcctgg agaaggcccc gccacttcca gtcgagcact cttcctgct     180 tccaccacaa caactcagcc aacttccact tcgactgctg aacctcttc cactaccaag    240 cctcctccag ctggatcggg aaccgctacg tattcaggca cccttactc tggggtcaac     300 ctttgggcca atagctatta ccgctctgaa gttaccaacc tcgctattcc taagttgagc    360
ggagccatgg ccactgctgc agcaaaggtc gcagatgttc cctcttttca gtggatggat    420
acttatgacc acatctcctt catggaggag tctttggccg acatccgcaa ggccaacaag    480
gctggcggta actatgccgg acagtttgtg gtgtatgact tgccggatcg cgattgcgct    540
gccgctgcct cgaatggcga atactctctt gacaaggatg caagaacaa atataaggcc    600 tatatcgcca agattaaggg tattctccag gactattccg ataccgat cattctggtt      660 attgagcctg actctcttgc caacatggtg accaacatga acgtcccaaa gtgtgccaat    720
gctgcttcag cctacaagga gctcaccatt cacgccctca aggagctgaa ccttccaaat    780
gtttccatgt atatcgacgc tggccatggt ggatggcttg ctggccggc aaaccttcct     840 ccggccgctc agctatacgg tcagctctac aaggatgcag gcaagccgtc tcgccttcgc    900
ggattggtca ccaatgtctc caactacaac gcctggaagc tatccagcaa gccagactac    960
acggagagca ccccaactac gacgagcag aagtacatcc acgctctgtc tcctcttctt    1020
gagcaggagg gctggcccgg tgccaagttc atcgtcgatc aaggtcgatc gggaaagcag   1080
cctaccggac agaaggcttg gggagactgg tgcaatgctc ccggcaccgg atttggtctc   1140
cgcccatccg caaacactgg ggacgccttg gtcgatgctt ttgtctgggt caagccaggc   1200
```

```
ggcgagtctg acggcaccag cgacaccagt gcggctcgat acgactacca ctgtggtatt   1260
gacggcgccg tcaagccggc gcctgaggct ggtacctggt tccaagccta ctttgagcag   1320
cttctcaaga acgcaaaccc atcgttcctg taa                                1353
```

<210> SEQ ID NO 28
<211> LENGTH: 450
<212> TYPE: PRT
<213> ORGANISM: Artificial Sequence
<220> FEATURE:
<223> OTHER INFORMATION: Clone 382A2

<400> SEQUENCE: 28

```
Ala Pro Leu Val Glu Glu Arg Gln Ala Cys Ala Ala Gln Trp Ala Gln
1               5                   10                  15

Cys Gly Gly Phe Ser Trp Asn Gly Ala Thr Cys Cys Gln Ser Gly Ser
            20                  25                  30

Tyr Cys Ser Lys Ile Asn Asp Tyr Tyr Ser Gln Cys Ile Pro Gly Glu
        35                  40                  45

Gly Pro Ala Thr Ser Lys Ser Ser Thr Leu Pro Ala Ser Thr Thr Thr
    50                  55                  60

Thr Gln Pro Thr Ser Thr Ser Thr Ala Gly Thr Ser Ser Thr Thr Lys
65                  70                  75                  80

Pro Pro Pro Ala Gly Ser Gly Thr Ala Thr Tyr Ser Gly Asn Pro Tyr
                85                  90                  95

Ser Gly Val Asn Leu Trp Ala Asn Ser Tyr Tyr Arg Ser Glu Val Thr
            100                 105                 110

Asn Leu Ala Ile Pro Lys Leu Ser Gly Ala Met Ala Thr Ala Ala Ala
        115                 120                 125

Lys Val Ala Asp Val Pro Ser Phe Gln Trp Met Asp Thr Tyr Asp His
    130                 135                 140

Ile Ser Phe Met Glu Glu Ser Leu Ala Asp Ile Arg Lys Ala Asn Lys
145                 150                 155                 160

Ala Gly Gly Asn Tyr Ala Gly Gln Phe Val Val Tyr Asp Leu Pro Asp
                165                 170                 175

Arg Asp Cys Ala Ala Ala Ala Ser Asn Gly Glu Tyr Ser Leu Asp Lys
            180                 185                 190

Asp Gly Lys Asn Lys Tyr Lys Ala Tyr Ile Ala Lys Ile Lys Gly Ile
        195                 200                 205

Leu Gln Asp Tyr Ser Asp Thr Arg Ile Ile Leu Val Ile Glu Pro Asp
    210                 215                 220

Ser Leu Ala Asn Met Val Thr Asn Met Asn Val Pro Lys Cys Ala Asn
225                 230                 235                 240

Ala Ala Ser Ala Tyr Lys Glu Leu Thr Ile His Ala Leu Lys Glu Leu
                245                 250                 255

Asn Leu Pro Asn Val Ser Met Tyr Ile Asp Ala Gly His Gly Gly Trp
            260                 265                 270

Leu Gly Trp Pro Ala Asn Leu Pro Ala Ala Gln Leu Tyr Gly Gln
            275                 280                 285

Leu Tyr Lys Asp Ala Gly Lys Pro Ser Arg Leu Arg Gly Leu Val Thr
    290                 295                 300

Asn Val Ser Asn Tyr Asn Ala Trp Lys Leu Ser Ser Lys Pro Asp Tyr
305                 310                 315                 320

Thr Glu Ser Asn Pro Asn Tyr Asp Glu Gln Lys Tyr Ile His Ala Leu
                325                 330                 335
```

```
Ser Pro Leu Leu Glu Gln Glu Gly Trp Pro Gly Ala Lys Phe Ile Val
            340                 345                 350

Asp Gln Gly Arg Ser Gly Lys Gln Pro Thr Gly Gln Lys Ala Trp Gly
        355                 360                 365

Asp Trp Cys Asn Ala Pro Gly Thr Gly Phe Gly Leu Arg Pro Ser Ala
    370                 375                 380

Asn Thr Gly Asp Ala Leu Val Asp Ala Phe Val Trp Val Lys Pro Gly
385                 390                 395                 400

Gly Glu Ser Asp Gly Thr Ser Asp Thr Ser Ala Ala Arg Tyr Asp Tyr
                405                 410                 415

His Cys Gly Ile Asp Gly Ala Val Lys Pro Ala Pro Glu Ala Gly Thr
            420                 425                 430

Trp Phe Gln Ala Tyr Phe Glu Gln Leu Leu Lys Asn Ala Asn Pro Ser
        435                 440                 445

Phe Leu
    450

<210> SEQ ID NO 29
<211> LENGTH: 1323
<212> TYPE: DNA
<213> ORGANISM: Gibberella zeae

<400> SEQUENCE: 29
gctcctgttg aagagcgtca gtcttgcagc aacggagtct ggtctcaatg tggtggtcag      60
aactggtccg gtactccttg ctgcaccagt ggaaacaagt gtgtcaaggt caacgacttc     120
tactcccagt gccagcctgg atctgcagac ccttctccca catccaccat tgtctccgcg     180
acgaccacca aggctactac tactggtagt ggaggctctg tcacctcgcc tcctcctgtt     240
gccaccaaca ccctttttc tggggtcgat ctgtgggcca ataactatta ccgctctgaa      300
gttagcactc tcgctattcc taagttgagc ggagccatgg ccactgctgc agcaaaggtc     360
gcagatgttc cctcttttca gtggatggat acttatgacc acatctcctt catggaggag     420
tctttggccg acatccgcaa ggccaacaag gctggcggta actatgccgg acagtttgtg     480
gtgtatgact gccggatcg cgattgcgct gccgctgcct cgaatggcga atactctctt      540
gacaaggatg gcaagaacaa atataaggcc tatatcgcca agattaaggg tattctccag     600
gactattccg ataccggat cattctggtt attgagcctg actctcttgc caacatggtg      660
accaacatga acgtcccaaa gtgtgccaat gctgcttcag cctacaagga gctcaccatt     720
cacgccctca aggagctgaa ccttccaaat gtttccatgt atatcgacgc tggccatggt     780
ggatggcttg gctggccggc aaaccttcct ccggccgctc agctatacgg tcagctctac     840
aaggatgcag gcaagccgtc tcgccttcgc ggattggtca ccaatgtctc caactacaac     900
gcctggaagc tatccagcaa gccagactac acggagagca ccccaactac gacgagcag      960 aagtacatcc acgctctgtc tcctcttctt gagcaggagg gctggcccgg tgccaagttc    1020
atcgtcgatc aaggtcgatc gggaaagcag cctaccggac agaaggcttg gggagactgg    1080
tgcaatgctc ccggcaccgg atttggtctc cgcccatccg caaacactgg gacgccttg    1140 gtcgatgctt ttgtctgggt caagccaggc ggcgagtctg acggcaccag cgacaccagt    1200
gcggctcgat acgactacca ctgtggtatt gacggcgccg tcaagccggc gcctgaggct    1260
ggtacctggt tccaagccta ctttgagcag cttctcaaga acgcaaaccc atcgttcctg    1320
taa                                                                  1323
```

<210> SEQ ID NO 30
<211> LENGTH: 440
<212> TYPE: PRT
<213> ORGANISM: Gibberella zeae

<400> SEQUENCE: 30

```
Ala Pro Val Glu Glu Arg Gln Ser Cys Ser Asn Gly Val Trp Ser Gln
  1               5                   10                  15

Cys Gly Gly Gln Asn Trp Ser Gly Thr Pro Cys Cys Thr Ser Gly Asn
                 20                  25                  30

Lys Cys Val Lys Val Asn Asp Phe Tyr Ser Gln Cys Gln Pro Gly Ser
             35                  40                  45

Ala Asp Pro Ser Pro Thr Ser Thr Ile Val Ser Ala Thr Thr Thr Lys
 50                  55                  60

Ala Thr Thr Thr Gly Ser Gly Gly Ser Val Thr Ser Pro Pro Pro Val
 65                  70                  75                  80

Ala Thr Asn Asn Pro Phe Ser Gly Val Asp Leu Trp Ala Asn Asn Tyr
                 85                  90                  95

Tyr Arg Ser Glu Val Ser Thr Leu Ala Ile Pro Lys Leu Ser Gly Ala
            100                 105                 110

Met Ala Thr Ala Ala Ala Lys Val Ala Asp Val Pro Ser Phe Gln Trp
        115                 120                 125

Met Asp Thr Tyr Asp His Ile Ser Phe Met Glu Glu Ser Leu Ala Asp
130                 135                 140

Ile Arg Lys Ala Asn Lys Ala Gly Gly Asn Tyr Ala Gly Gln Phe Val
145                 150                 155                 160

Val Tyr Asp Leu Pro Asp Arg Asp Cys Ala Ala Ala Ser Asn Gly
                165                 170                 175

Glu Tyr Ser Leu Asp Lys Asp Gly Lys Asn Lys Tyr Lys Ala Tyr Ile
            180                 185                 190

Ala Lys Ile Lys Gly Ile Leu Gln Asp Tyr Ser Asp Thr Arg Ile Ile
        195                 200                 205

Leu Val Ile Glu Pro Asp Ser Leu Ala Asn Met Val Thr Asn Met Asn
210                 215                 220

Val Pro Lys Cys Ala Asn Ala Ala Ser Ala Tyr Lys Glu Leu Thr Ile
225                 230                 235                 240

His Ala Leu Lys Glu Leu Asn Leu Pro Asn Val Ser Met Tyr Ile Asp
            245                 250                 255

Ala Gly His Gly Gly Trp Leu Gly Trp Pro Ala Asn Leu Pro Pro Ala
        260                 265                 270

Ala Gln Leu Tyr Gly Gln Leu Tyr Lys Asp Ala Gly Lys Pro Ser Arg
    275                 280                 285

Leu Arg Gly Leu Val Thr Asn Val Ser Asn Tyr Asn Ala Trp Lys Leu
290                 295                 300

Ser Ser Lys Pro Asp Tyr Thr Glu Ser Asn Pro Asn Tyr Asp Glu Gln
305                 310                 315                 320

Lys Tyr Ile His Ala Leu Ser Pro Leu Leu Glu Gln Glu Gly Trp Pro
            325                 330                 335

Gly Ala Lys Phe Ile Val Asp Gln Gly Arg Ser Gly Lys Gln Pro Thr
        340                 345                 350

Gly Gln Lys Ala Trp Gly Asp Trp Cys Asn Ala Pro Gly Thr Gly Phe
    355                 360                 365

Gly Leu Arg Pro Ser Ala Asn Thr Gly Asp Ala Leu Val Asp Ala Phe
370                 375                 380
```

```
Val Trp Val Lys Pro Gly Gly Glu Ser Asp Gly Thr Ser Asp Thr Ser
385                 390                 395                 400

Ala Ala Arg Tyr Asp Tyr His Cys Gly Ile Asp Gly Ala Val Lys Pro
            405                 410                 415

Ala Pro Glu Ala Gly Thr Trp Phe Gln Ala Tyr Phe Glu Gln Leu Leu
        420                 425                 430

Lys Asn Ala Asn Pro Ser Phe Leu
    435                 440
```

<210> SEQ ID NO 31
<211> LENGTH: 1353
<212> TYPE: DNA
<213> ORGANISM: Nectria haematococca

<400> SEQUENCE: 31

```
gcccctcttg ttgaggagcg ccaggcttgc gctgcccaat gggcccagtg tggtggcttc      60
agctggaatg gtgctacctg ctgccagtct ggtagctact gcagcaagat caacgactat     120
tactctcagt gcattcctgg agaaggcccc gccacttcca gtcgagcac tcttcctgct      180
tccaccacaa caactcagcc aacttccact tcgactgctg aacctcttc cactaccaag      240
cctcctccag ctggatcggg aaccgctacg tattcaggca acccttactc tggggtcaac     300
ctttgggcca atagctatta ccgctctgaa gttaccaacc tcgctattcc taagttgagc     360
ggagccatgg ccactgctgc agcaaaggtc gcagatgttc cctcttatca gtggatggat     420
tctttcgacc acatctccct catggaggac accttggtcg acatccgcaa ggccaacctg     480
gctggcggta actatgccgg acagtttgtg gtgtatgact gccggatcg cgattgcgct     540
gccgccgcct cgaatggcga atactctctc gacaatgatg cgccaacaa atataagaac     600
tatatccaaa ccattaagaa gattatccag agctattccg atatccggat actcctggtt     660
attgagcctg actctcttgc caacctggtg accaacatgg atgtcgccaa gtgtgccaag     720
gctcatgatg cctacatcag cctgacgaac tacgccgtca gaactgaa ccttccaaat      780
gttgcgatgt atttggacgc tggccatgca ggatggcttg gctggccggc aaaccaaggc     840
ccggccgcta aactatttgc aagcatctac aaggatgcag gcaagccggc cgctcttcgc     900
ggattggcaa ccaatgtcgc caactacaac gcctggagcc tcagcagcgc tccaccttac     960
acgcaaggcg cctctatcta cgacgagaag agcttcatcc acgctatggg acctcttctt    1020
gagcagaatg gctggcctgg tgcccacttc atcactgatc aaggtcgatc gggaaagcag    1080
cctaccggac agatccagtg gggagactgg tgcaattcca agggcaccgg atttggtatt    1140
cgcccatccg caaacactgg ggactcgttg ctggatgctt ttgtctgggt caagccaggc    1200
ggcgagtctg acggcaccag cgacaccagt gcgacccgat acgactacca ctgtggtgct    1260
tctgccgcct tgcaaccggc gcctgaggct ggtacctggt tccaagccta ctttgagcag    1320
cttctcacaa acgcaaaccc atcgttcctg taa                                 1353
```

<210> SEQ ID NO 32
<211> LENGTH: 450
<212> TYPE: PRT
<213> ORGANISM: Nectria haematococca

<400> SEQUENCE: 32

```
Ala Pro Leu Val Glu Glu Arg Gln Ala Cys Ala Ala Gln Trp Ala Gln
1               5                   10                  15

Cys Gly Gly Phe Ser Trp Asn Gly Ala Thr Cys Cys Gln Ser Gly Ser
            20                  25                  30
```

```
Tyr Cys Ser Lys Ile Asn Asp Tyr Tyr Ser Gln Cys Ile Pro Gly Glu
            35                  40                  45

Gly Pro Ala Thr Ser Lys Ser Ser Thr Leu Pro Ala Ser Thr Thr Thr
         50                  55                  60

Thr Gln Pro Thr Ser Thr Ser Thr Ala Gly Thr Ser Ser Thr Thr Lys
 65                  70                  75                  80

Pro Pro Pro Ala Gly Ser Gly Thr Ala Thr Tyr Ser Gly Asn Pro Tyr
                 85                  90                  95

Ser Gly Val Asn Leu Trp Ala Asn Ser Tyr Tyr Arg Ser Glu Val Thr
                100                 105                 110

Asn Leu Ala Ile Pro Lys Leu Ser Gly Ala Met Ala Thr Ala Ala Ala
            115                 120                 125

Lys Val Ala Asp Val Pro Ser Tyr Gln Trp Met Asp Ser Phe Asp His
        130                 135                 140

Ile Ser Leu Met Glu Asp Thr Leu Val Asp Ile Arg Lys Ala Asn Leu
145                 150                 155                 160

Ala Gly Gly Asn Tyr Ala Gly Gln Phe Val Val Tyr Asp Leu Pro Asp
                165                 170                 175

Arg Asp Cys Ala Ala Ala Ser Asn Gly Glu Tyr Ser Leu Asp Asn
            180                 185                 190

Asp Gly Ala Asn Lys Tyr Lys Asn Tyr Ile Gln Thr Ile Lys Lys Ile
                195                 200                 205

Ile Gln Ser Tyr Ser Asp Ile Arg Ile Leu Val Ile Glu Pro Asp
            210                 215                 220

Ser Leu Ala Asn Leu Val Thr Asn Met Asp Val Ala Lys Cys Ala Lys
225                 230                 235                 240

Ala His Asp Ala Tyr Ile Ser Leu Thr Asn Tyr Ala Val Thr Glu Leu
                245                 250                 255

Asn Leu Pro Asn Val Ala Met Tyr Leu Asp Ala Gly His Ala Gly Trp
            260                 265                 270

Leu Gly Trp Pro Ala Asn Gln Gly Pro Ala Ala Lys Leu Phe Ala Ser
        275                 280                 285

Ile Tyr Lys Asp Ala Gly Lys Pro Ala Ala Leu Arg Gly Leu Ala Thr
    290                 295                 300

Asn Val Ala Asn Tyr Asn Ala Trp Ser Leu Ser Ser Ala Pro Pro Tyr
305                 310                 315                 320

Thr Gln Gly Ala Ser Ile Tyr Asp Glu Lys Ser Phe Ile His Ala Met
                325                 330                 335

Gly Pro Leu Leu Glu Gln Asn Gly Trp Pro Gly Ala His Phe Ile Thr
            340                 345                 350

Asp Gln Gly Arg Ser Gly Lys Gln Pro Thr Gly Gln Ile Gln Trp Gly
        355                 360                 365

Asp Trp Cys Asn Ser Lys Gly Thr Gly Phe Gly Ile Arg Pro Ser Ala
    370                 375                 380

Asn Thr Gly Asp Ser Leu Leu Asp Ala Phe Val Trp Val Lys Pro Gly
385                 390                 395                 400

Gly Glu Ser Asp Gly Thr Ser Asp Thr Ser Ala Thr Arg Tyr Asp Tyr
                405                 410                 415

His Cys Gly Ala Ser Ala Ala Leu Gln Pro Ala Pro Glu Ala Gly Thr
            420                 425                 430

Trp Phe Gln Ala Tyr Phe Glu Gln Leu Leu Thr Asn Ala Asn Pro Ser
        435                 440                 445
```

-continued

```
Phe Leu
    450

<210> SEQ ID NO 33
<211> LENGTH: 54
<212> TYPE: DNA
<213> ORGANISM: Artificial Sequence
<220> FEATURE:
<223> OTHER INFORMATION: peptide signal de CBH2

<400> SEQUENCE: 33
atgattgtcg gcattctcac cacgctggct acgctggcca cactcgcagc tagt          54

<210> SEQ ID NO 34
<211> LENGTH: 99
<212> TYPE: DNA
<213> ORGANISM: Saccharomyces cerevisiae

<400> SEQUENCE: 34
atgaagcttt ccaccatcct tttcacagcc tgcgctaccc tggctgccgc cctcccttcc    60
cccatcactc cttctgaggc cgcagttctg cagaagagg                           99

<210> SEQ ID NO 35
<211> LENGTH: 33
<212> TYPE: PRT
<213> ORGANISM: Saccharomyces cerevisiae

<400> SEQUENCE: 35

Met Lys Leu Ser Thr Ile Leu Phe Thr Ala Cys Ala Thr Leu Ala Ala
1               5                   10                  15

Ala Leu Pro Ser Pro Ile Thr Pro Ser Glu Ala Ala Val Leu Gln Lys
            20                  25                  30

Arg
```